United States Patent
Sumiyoshi et al.

(10) Patent No.: US 9,901,513 B2
(45) Date of Patent: *Feb. 27, 2018

(54) DRUG SOLUTION HAVING REDUCED DISSOLVED OXYGEN CONTENT, METHOD OF PRODUCING THE SAME AND DRUG SOLUTION CONTAINING UNIT HAVING REDUCED DISSOLVED OXYGEN CONTENT

(75) Inventors: Nobuaki Sumiyoshi, Naruto (JP); Isamu Tateishi, Naruto (JP); Hitoshi Mori, Tokushima (JP); Yasushi Morimoto, Naruto (JP)

(73) Assignee: OTSUKA PHARMACEUTICAL FACTORY, INC., Tokushima (JP)

( * ) Notice: Subject to any disclaimer, the term of this patent is extended or adjusted under 35 U.S.C. 154(b) by 1028 days.

This patent is subject to a terminal disclaimer.

(21) Appl. No.: 12/447,101

(22) PCT Filed: Oct. 25, 2007

(86) PCT No.: PCT/JP2007/070828
§ 371 (c)(1),
(2), (4) Date: Dec. 10, 2009

(87) PCT Pub. No.: WO2008/050837
PCT Pub. Date: May 2, 2008

(65) Prior Publication Data
US 2010/0092446 A1  Apr. 15, 2010

(30) Foreign Application Priority Data

Oct. 27, 2006  (JP) .................................. 2006-293009
Oct. 27, 2006  (JP) .................................. 2006-293010
Oct. 27, 2006  (JP) .................................. 2006-293011

(51) Int. Cl.
*A61J 1/00*  (2006.01)
*A61K 31/07*  (2006.01)
(Continued)

(52) U.S. Cl.
CPC ...... *A61J 1/10* (2013.01); *A61K 9/08* (2013.01); *A61J 1/2093* (2013.01)

(58) Field of Classification Search
None
See application file for complete search history.

(56) References Cited

U.S. PATENT DOCUMENTS 4,414,230 A   11/1983  Hanabata et al.
4,561,108 A * 12/1985  Kamp ................ B65D 33/2541
                                                        24/339

(Continued)

FOREIGN PATENT DOCUMENTS

CN     1218385        2/1999
EP     1 245 217 A2   10/2002
(Continued)

OTHER PUBLICATIONS

International Preliminary Report on Patentability issued Apr. 28, 2009 in corresponding International Application No. PCT/JP2007/070828.

(Continued)

*Primary Examiner* — Blaine Lankford
*Assistant Examiner* — Lauren K Van Buren
(74) *Attorney, Agent, or Firm* — Finnegan, Henderson, Farabow, Garrett & Dunner, LLP

(57) ABSTRACT

A reduced-dissolved-oxygen-content drug solution produced by filling and sealing the drug solution in a drug solution container (15) formed of a plastic material having an oxygen permeability of not lower than 200 cm$^3$/m$^2$·24 h·atm at 25° C. at 60% RH within 12 hours after a steam sterilization process or a hot water sterilization process and having a steady-state oxygen permeability of not higher than 100 cm$^3$/m$^2$·24 h·atm at 25° C. at 60% RH, subjecting the drug solution container to the steam sterilization process or (Continued)

the hot water sterilization process, and storing the drug solution container in an environment having deoxidization means for reducing the dissolved oxygen concentration of the drug solution to not higher than 2 ppm when the oxygen permeability of the plastic material reaches the steady-state level.

21 Claims, 3 Drawing Sheets

(51) Int. Cl.
*A61J 1/10* (2006.01)
*A61K 9/08* (2006.01)
*A61J 1/20* (2006.01)

(56) References Cited

U.S. PATENT DOCUMENTS

| | | | |
|---|---|---|---|
| 4,657,540 A | 4/1987 | Iwamoto et al. | |
| 5,032,632 A * | 7/1991 | Saxton | 524/139 |
| 5,132,149 A | 7/1992 | Kotani et al. | |
| 5,728,681 A * | 3/1998 | Kido | A61J 1/2093 |
| | | | 514/167 |
| 5,766,751 A | 6/1998 | Kotani et al. | |
| 5,772,960 A | 6/1998 | Ito et al. | |
| 6,007,529 A | 12/1999 | Gustafsson et al. | |
| 6,398,771 B1 * | 6/2002 | Gustafsson et al. | 604/410 |
| 6,713,137 B1 | 3/2004 | Andersson et al. | |
| 6,777,052 B2 * | 8/2004 | Kai | A61J 1/00 |
| | | | 206/438 |
| 6,996,995 B2 * | 2/2006 | Voute et al. | 62/62 |
| 2002/0192411 A1 | 12/2002 | Kai et al. | |
| 2004/0050744 A1 | 3/2004 | Hama et al. | |
| 2005/0177128 A1 * | 8/2005 | Nagao | A61J 1/2093 |
| | | | 604/411 |
| 2006/0229583 A1 | 10/2006 | Nagao et al. | |
| 2009/0032426 A1 | 2/2009 | Tateishi et al. | |

FOREIGN PATENT DOCUMENTS

| | | |
|---|---|---|
| EP | 1 396 249 A2 | 3/2004 |
| EP | 1 875 889 A1 | 1/2008 |
| GB | 2 025 895 A | 1/1980 |
| JP | 63-275346 | 11/1988 |
| JP | 02-200266 | 8/1990 |
| JP | 02-258339 | 10/1990 |
| JP | 04-276253 | 10/1992 |
| JP | 5-31154 | 2/1993 |
| JP | 05-064653 | 3/1993 |
| JP | 07-067936 | 3/1995 |
| JP | 09-182778 | 7/1997 |
| JP | 10-80464 | 3/1998 |
| JP | 10-201818 | 8/1998 |
| JP | 11-285520 | 10/1999 |
| JP | 2000-033674 | 2/2000 |
| JP | 2002-160771 | 6/2002 |
| JP | 2002-173171 | 6/2002 |
| JP | 2003-010287 | 1/2003 |
| JP | 1177640 | 6/2003 |
| JP | 2003-205014 | 7/2003 |
| JP | 2005-152618 | 6/2005 |
| JP | 2005-523772 | 8/2005 |
| JP | 2005-304911 | 11/2005 |
| JP | 2005304911 * | 11/2005 |
| JP | 2006-20657 | 1/2006 |
| JP | 2008 117586 | 5/2006 |
| JP | 2006-187429 | 7/2006 |
| JP | 2006-217975 | 8/2006 |
| WO | WO 88/08694 | 11/1988 |
| WO | WO 01/62202 A1 | 8/2001 |
| WO | WO 03/018312 A1 | 3/2003 |
| WO | WO 03/037083 | 5/2003 |
| WO | WO 03/092574 A1 | 11/2003 |
| WO | WO 2004/093775 A1 | 11/2004 |
| WO | WO 2005/004902 A1 | 1/2005 |
| WO | WO 2006/118034 A1 | 11/2006 |

OTHER PUBLICATIONS

Decision of Grant of Patent dated Dec. 6, 2012 in related Japanese patent application 2011-172243: pp. 1-3.
European Search Report for EP Application No. 06 74 5438 dated Oct. 29, 2013.
European Search Report for EP Application No. 07 83 0562 dated Nov. 25, 2013.

* cited by examiner

DRUG SOLUTION HAVING REDUCED DISSOLVED OXYGEN CONTENT, METHOD OF PRODUCING THE SAME AND DRUG SOLUTION CONTAINING UNIT HAVING REDUCED DISSOLVED OXYGEN CONTENT

TECHNICAL FIELD

The present invention relates to a drug solution with a reduced dissolved oxygen content, a production method therefor, and a drug solution containing pack with a reduced dissolved oxygen content.

BACKGROUND ART

Nutrition of a patient who has poor oral intake is typically achieved by intravenous administration of an infusion solution containing a saccharide, amino acids, vitamins, electrolytes, a fat emulsion, micronutrient metal elements and the like. The amino acids and the vitamins contained in the infusion solution are susceptible to oxidation. Further, a polyolefin resin, which is well-known as a material for the infusion container, is permeable to oxygen. Therefore, the infusion solution suffers from oxidation of oxidation-prone components such as the amino acids and the vitamins during storage thereof.

In order to stably store the infusion solution containing the oxidation-prone components, Patent Document 1 proposes a packaged infusion solution container, which includes a gas-permeable primary medical container which contains an infusion solution of an amino acid containing aqueous solution, and a substantially oxygen-impermeable secondary package container which contains the primary medical container containing the infusion solution together with an oxygen scavenger. Further, Patent Document 2 proposes a film for a drug container, which includes a plastic film and an inorganic compound film formed on at least one surface of the plastic film, and has an oxygen permeability of not higher than 1 cc/m²·24 hr·atm, a water vapor permeability of not higher than 1 g/m²·24 hr·atm, a light transmittance of not lower than 80% and a hue b-value of not greater than 5.

Further, Patent Document 3 discloses a packaged container which includes: a gas-barrier infusion solution container of a resin including a flexible container wall having at least an outlet port and composed of a multilayer film including an inner layer, a polyvinyl alcohol intermediate layer and an outer layer, the innermost layer being a polyolefin layer having a thickness of 50 to 800 μm, the outer layer being arranged so that the water vapor permeability $S_o$ thereof (g/m²·24 hrs at a temperature of 40° C. at a humidity of 90% RH) is not less than twice the water vapor permeability $S_i$ of the inner layer (g/m²·24 hrs at a temperature of 40° C. at a humidity of 90% RH); and a package containing the infusion solution container together with a desiccating agent. With this arrangement, water vapor is speedily expelled out of the outer layer of the infusion container. Therefore, the water vapor contents of the outer layer and the polyvinyl alcohol layer adjoining each other can be reduced by the desiccating agent provided outside the container after an autoclave sterilization process. As a result, the gas barrier property of the polyvinyl alcohol layer is almost completely recovered within 24 hours. Further, water vapor transmitted through the innermost layer from the inside of the infusion solution container to reach the polyvinyl alcohol layer is speedily expelled out of the polyvinyl alcohol layer through the outer layer. Therefore, the polyvinyl alcohol layer is free from deterioration of the gas barrier property.

Patent Document 1: JP-A-SHO63(1988)-275346
Patent Document 2: JP-A-HEI11(1999)-285520
Patent Document 3: JP-A-HEI10(1998)-80464

DISCLOSURE OF THE INVENTION

Problems to be Solved by the Invention

Where the primary container of the packaged infusion solution container is permeable to oxygen as disclosed in Patent Document 1, it is impossible to prevent the oxidative degradation of the infusion solution in the primary container when the primary container is allowed to stand after the secondary container is unsealed. In addition, where another drug is injected into the primary container, proliferation of bacteria inadvertently entering the primary container is promoted by oxygen penetrated into the primary container from the outside.

The film for the drug container disclosed in Patent Document 2 is excellent in oxygen barrier property. Therefore, where oxygen is present in a head space of the container or a greater amount of oxygen is dissolved in the drug solution sealed in the container, it is impossible to prevent the oxidative degradation of the drug solution and the proliferation of aerobic bacteria. A process for reducing the amount of the oxygen dissolved in the drug solution before the sealing of the container and a process for replacing the oxygen present in the head space with an inert gas such as nitrogen are troublesome, disadvantageously leading to higher costs. Further, the film for the drug container has insufficient flexibility. Therefore, there is a possibility that a pin hole occurs in the film due to an impact applied to the film, for example, during transportation of the drug container.

In the case of the infusion solution container disclosed in Patent Document 3, as described above, the amount of the water vapor contained in the polyvinyl alcohol layer is reduced by the desiccating agent provided outside the container, so that the gas barrier property of the polyvinyl alcohol layer can be maintained. However, no consideration is given to oxygen remaining in the infusion container after the autoclave sterilization process. Therefore, it is impossible to prevent the oxidative degradation of the drug solution and the proliferation of the aerobic bacteria which may occur due to the oxygen remaining in the infusion solution container.

It is an object of the present invention to provide a drug solution which has a reduced dissolved oxygen content, and is less susceptible to oxidative degradation and highly stable over time, and to provide a production method therefor.

It is another object of the present invention to provide a drug solution containing pack which is capable of maintaining the dissolved oxygen content of a drug solution at a reduced level and suppressing oxidative degradation of the drug solution, and is highly stable over time.

Means for Solving the Problems

According to the present invention to achieve the aforementioned objects, there is provided a drug solution with a reduced dissolved oxygen content, the drug solution being contained and sealed in a drug solution container formed of a plastic material having an oxygen permeability of not lower than 200 cm³/m²·24 h·atm at a temperature of 25° C. at a humidity of 60% RH within 12 hours after a steam sterilization process or a hot water sterilization process and having a steady-state oxygen permeability of not higher than 100 cm$^3$/m$^2$·24 h·atm at a temperature of 25° C. at a humidity of 60% RH, the drug solution having been subjected to the steam sterilization process or the hot water sterilization process, the drug solution having a dissolved oxygen concentration of not higher than 2 ppm when the oxygen permeability of the plastic material reaches the steady-state level after the steam sterilization process or the hot water sterilization process.

The drug solution container in which the reduced-dissolved-oxygen-content drug solution is contained and sealed is formed of the plastic material having a high oxygen permeability, i.e., an oxygen permeability of 200 cm$^3$/m$^2$·24 h·atm or higher (at a temperature of 25° C. at a humidity of 60% RH) within 12 hours after the steam sterilization process or the hot water sterilization process and having a low steady-state oxygen permeability, i.e., a steady-state oxygen permeability of 100 cm$^3$/m$^2$·24 h·atm or lower (at a temperature of 25° C. at a humidity of 60% RH). Therefore, a process for reducing the amount of oxygen dissolved in the drug solution and the amount of oxygen remaining in the drug solution container can be performed outside the drug solution container by utilizing the higher oxygen permeability of the plastic material after the drug solution container is subjected to the steam sterilization process or the hot water sterilization process before the oxygen permeability of the plastic material reaches the steady-state level. By utilizing the fact that the oxygen permeability of the plastic material is very low after the oxygen permeability of the plastic material reaches the steady-state level, an increase in the dissolved oxygen content of the drug solution can be suppressed. Further, the dissolved oxygen content of the reduced-dissolved-oxygen-content drug solution can be maintained at a very low level for along period of time by reducing the dissolved oxygen content of the drug solution to not higher than 2 ppm after the steam sterilization process or the hot water sterilization process or by preliminarily reducing the dissolved oxygen content of the drug solution to not higher than 2 ppm. This prevents the oxidative degradation of the drug solution.

The reduced-dissolved-oxygen-content drug solution according to the present invention is preferably stored in an environment having deoxidization means after the steam sterilization process or the hot water sterilization process.

In this case, the oxygen dissolved in the drug solution and the oxygen remaining in the drug solution container can be removed by the deoxidization means outside the drug solution container when the plastic material of the drug solution container has a higher oxygen permeability after the steam sterilization process or the hot water sterilization process. Further, it is possible to change the oxygen permeability of the plastic material of the drug solution container to the steady-state level while preventing intrusion of oxygen into the drug solution container by storing the drug solution container in the environment having the deoxidization means.

The reduced-dissolved-oxygen-content drug solution according to the present invention is preferably an oxidation-prone drug solution and, more specifically, includes at least one solution selected from the group consisting of an amino acid containing solution, a vitamin containing saccharide solution and a lipid-soluble vitamin containing solution.

In the reduced-dissolved-oxygen-content drug solution according to the present invention, the amino acid containing solution preferably contains at least one amino acid selected from the group consisting of L-leucine, L-isoleucine, L-valine, L-lysine, L-threonine, L-tryptophan, L-methionine, L-cysteine, L-phenylalanine, L-tyrosine, L-arginine, L-histidine, L-alanine, L-proline, L-serine, L-glycine, L-aspartic acid and L-glutamic acid.

In the reduced-dissolved-oxygen-content drug solution according to the present invention, the vitamin containing saccharide solution preferably contains a saccharide, and a water-soluble vitamin selected from the group consisting of vitamin B$_1$, vitamin B$_2$, vitamin B$_6$, vitamin B$_{12}$, Vitamin C, folic acid, niacin, biotin and a pantothenic compound.

In the reduced-dissolved-oxygen-content drug solution according to the present invention, the lipid-soluble vitamin containing solution preferably contains at least one lipid-soluble vitamin selected from the group consisting of vitamin A, vitamin D, vitamin E and vitamin K.

According to the present invention to achieve the aforementioned objects, a production method for a reduced-dissolved-oxygen-content drug solution includes the steps of: filling and sealing a drug solution in a drug solution container formed of a plastic material having an oxygen permeability of not lower than 200 cm$^3$/m$^2$·24 h·atm at a temperature of 25° C. at a humidity of 60% RH within 12 hours after a steam sterilization process or a hot water sterilization process and having a steady-state oxygen permeability of not higher than 100 cm$^3$/m$^2$·24 h·atm at a temperature of 25° C. at a humidity of 60% RH; subjecting the drug solution container to a steam sterilization process or a hot water sterilization process; and reducing the dissolved oxygen concentration of the drug solution to not higher than 2 ppm by storing the drug solution container in an environment having deoxidization means until the oxygen permeability of the plastic material reaches the steady-state level.

In the production method for the reduced-dissolved-oxygen-content drug solution, the drug solution container in which the drug solution is filled and sealed is composed of the plastic material having a high oxygen permeability, i.e., an oxygen permeability of 200 cm$^3$/m$^2$·24 h·atm or higher (at a temperature of 25° C. at a humidity of 60% RH) within 12 hours after the steam sterilization process or the hot water sterilization process and having a low steady-state oxygen permeability, i.e., a steady-state oxygen permeability of 100 cm$^3$/m$^2$·24 h·atm or lower (at a temperature of 25° C. at a humidity of 60% RH). Therefore, the amount of oxygen dissolved in the drug solution and the amount of oxygen remaining in the drug solution container can be efficiently reduced outside the drug solution container by storing the drug solution container in the environment having the deoxidization means after the drug solution container in which the drug solution is filled and sealed is subjected to the steam sterilization process or the hot water sterilization process before the oxygen permeability of the plastic material reaches the steady-state level, i.e., when the oxygen permeability of the plastic material is kept higher. By utilizing the fact that the oxygen permeability of the plastic material is very low after the oxygen permeability of the plastic material reaches the steady-state level, an increase in the dissolved oxygen content of the drug solution can be suppressed. According to the production method for the reduced-dissolved-oxygen-content drug solution, the amount of oxygen dissolved in the drug solution filled and sealed in the drug solution container is reduced to a very low level, i.e., 2 ppm or lower, and maintained at the very low level.

In the inventive production method for the reduced-dissolved-oxygen-content drug solution, the environment having the deoxidization means is preferably an environment enclosed in an outer package provided with the deoxidization means and having an oxygen barrier property.

In this case, the oxygen dissolved in the drug solution filled and sealed in the drug solution container and the oxygen remaining in the drug solution container can be more efficiently removed by the deoxidization means outside the drug solution container.

In the inventive production method for the reduced-dissolved-oxygen-content drug solution, the deoxidization means is preferably an oxygen scavenger.

According to the present invention to achieve the aforementioned objects, a drug solution containing pack with a reduced dissolved oxygen content includes a drug solution container formed of a plastic material having an oxygen permeability of not lower than 200 $cm^3/m^2 \cdot 24$ h·atm at a temperature of 25° C. at a humidity of 60% RH within 12 hours after a steam sterilization process or a hot water sterilization process and having a steady-state oxygen permeability of not higher than 100 $cm^3/m^2 \cdot 24$ h·atm at a temperature of 25° C. at a humidity of 60% RH, and a drug solution contained and sealed in the drug solution container. The drug solution contained and sealed in the drug solution container has been subjected to the steam sterilization process or the hot water sterilization process, and to a deoxidization process for reducing the dissolved oxygen concentration of the drug solution to not higher than 2 ppm when the oxygen permeability of the plastic material reaches the steady-state level after the steam sterilization process or the hot water sterilization process.

In the reduced-dissolved-oxygen-content drug solution containing pack, the drug solution container in which the drug solution is contained and sealed is formed of the plastic material having a high oxygen permeability, i.e., an oxygen permeability of 200 $cm^3/m^2 \cdot 24$ h·atm or higher (at a temperature of 25° C. at a humidity of 60% RH), within 12 hours after the steam sterilization process or the hot water sterilization process and having a low steady-state oxygen permeability, i.e., a steady-state oxygen permeability of 100 $cm^3/m^2 \cdot 24$ h·atm or lower (at a temperature of 25° C. at a humidity of 60% RH). Therefore, a process for reducing the amount of oxygen dissolved in the drug solution and the amount of oxygen remaining in the drug solution container can be performed outside the drug solution container by utilizing the higher oxygen permeability of the plastic material after the drug solution container is subjected to the steam sterilization process or the hot water sterilization process before the oxygen permeability of the plastic material reaches the steady-state level. By utilizing the fact that the oxygen permeability of the plastic material is very low after the oxygen permeability of the plastic material reaches the steady-state level, an increase in the dissolved oxygen content of the drug solution can be suppressed. Further, the dissolved oxygen content of the drug solution of the drug solution containing pack can be maintained at a very low level for a long period of time by reducing the dissolved oxygen content of the drug solution of the drug solution containing pack to not higher than 2 ppm after the steam sterilization process or the hot water sterilization process or by preliminarily reducing the dissolved oxygen content of the drug solution to be contained in the drug solution container to not higher than 2 ppm. This prevents the oxidative degradation of the drug solution.

The inventive reduced-dissolved-oxygen-content drug solution containing pack is preferably stored in an environment having deoxidization means after the steam sterilization process or the hot water sterilization process.

In this case, the oxygen dissolved in the drug solution and the oxygen remaining in the drug solution containing pack can be removed by the deoxidization means outside the drug solution containing pack when the plastic material of the drug solution container has a higher oxygen permeability after the steam sterilization process or the hot water sterilization process. Further, it is possible to change the oxygen permeability of the plastic material of the drug solution container to the steady-state level while preventing intrusion of oxygen into the drug solution containing pack by storing the drug solution containing pack in the environment having the deoxidization means.

In the reduced-dissolved-oxygen-content drug solution containing pack according to the present invention, the drug solution is preferably an oxidation-prone drug solution and, more specifically, includes at least one solution selected from the group consisting of an amino acid containing solution, a vitamin containing saccharide solution and a lipid-soluble vitamin containing solution.

In the reduced-dissolved-oxygen-content drug solution containing pack according to the present invention, the drug solution container preferably includes a plurality of container portions isolated from each other by a removable partition. An amino acid containing solution is contained in one of the container portions, and a saccharide solution is contained in another one of the container portions.

In the reduced-dissolved-oxygen-content drug solution containing pack according to the present invention, the drug solution container preferably includes a plurality of container portions isolated from each other by a removable partition, and one of the container portions is a small bag provided in another one of the container portions.

In this case, a lipid-soluble vitamin containing solution or a fat emulsion is preferably contained in the small bag. Alternatively, the small bag may be partitioned into two compartments. A lipid-soluble vitamin containing solution is contained in one of the two compartments, and a micronutrient metal element drug solution is contained in the other compartment.

In the reduced-dissolved-oxygen-content drug solution containing pack according to the present invention, the amino acid containing solution preferably contains at least one amino acid selected from the group consisting of L-leucine, L-isoleucine, L-valine, L-lysine, L-threonine, L-tryptophan, L-methionine, L-cysteine, L-phenylalanine, L-tyrosine, L-arginine, L-histidine, L-alanine, L-proline, L-serine, L-glycine, L-aspartic acid and L-glutamic acid.

The vitamin containing saccharide solution preferably contains a saccharide, and at least one water-soluble vitamin selected from the group consisting of vitamin $B_1$, vitamin $B_2$, vitamin $B_6$, vitamin $B_{12}$, vitamin C, folic acid, niacin, biotin and a pantothenic compound.

The lipid-soluble vitamin containing solution preferably contains at least one lipid-soluble vitamin selected from the group consisting of vitamin A, vitamin D, vitamin E and vitamin K.

The micronutrient metal element drug solution preferably contains at least one element selected from the group consisting of iron, manganese, zinc, copper, selenium, molybdenum, cobalt and chromium.

In the reduced-dissolved-oxygen-content drug solution containing pack according to the present invention, the plurality of container portions isolated from each other by the removable partition preferably includes two container portions disposed in opposed relation on opposite sides of the removable partition, and a small bag disposed in one of the two container portions. The small bag is further partitioned into two compartments. An amino acid containing solution which contains at least one amino acid selected from the group consisting of L-leucine, L-isoleucine, L-valine, L-lysine, L-threonine, L-tryptophan, L-methionine, L-cysteine, L-phenylalanine, L-tyrosine, L-arginine, L-histidine, L-alanine, L-proline, L-serine, L-glycine, L-aspartic acid and L-glutamic acid is contained in the one container portion, and a vitamin containing saccharide solution which contains a saccharide and at least one water-soluble vitamin selected from the group consisting of vitamin $B_1$, vitamin $B_2$, vitamin $B_6$, vitamin $B_{12}$, vitamin C, folic acid, niacin, biotin and a pantothenic compound is contained in the other container portion. A lipid-soluble vitamin containing solution which contains at least one lipid-soluble vitamin selected from the group consisting of vitamin A, vitamin D, vitamin E and vitamin K is contained in one of the compartments of the small bag, and a micronutrient metal element drug solution which contains at least one element selected from the group consisting of iron, manganese, zinc, copper, selenium, molybdenum, cobalt and chromium is contained in the other compartment of the small bag.

In this case, a solution mixture obtained by mixing the solutions contained in the two container portions and the two compartments preferably contains 0.4 to 20.0 g/L of L-leucine, 0.2 to 14.0 g/L of L-isoleucine, 0.1 to 16.0 g/L of L-valine, 0.2 to 14.0 g/L of L-lysine, 0.1 to 8.0 g/L of L-threonine, 0.04 to 3.0 g/L of L-tryptophan, 0.1 to 8.0 g/L of L-methionine, 0.01 to 2.0 g/L of L-cysteine, 0.2 to 12.0 g/L of L-phenylalanine, 0.01 to 2 g/L of L-tyrosine, 0.2 to 14.0 g/L of L-arginine, 0.1 to 8.0 g/L of L-histidine, 0.2 to 14.0 g/L of L-alanine, 0.1 to 10.0 g/L of L-proline, 0.1 to 6.0 g/L of L-serine, 0.1 to 12.0 g/L of L-glycine, 0.01 to 4.0 g/L of L-aspartic acid, 0 to 6.0 g/L of L-glutamic acid, 20 to 800 g/L of glucose, 400 to 6500 IU/L of vitamin A, 0.5 to 10.0 µg/L of cholecalciferol as vitamin D, 1.0 to 20.0 mg/L of tocopherol acetate as vitamin E, 0.2 to 4.0 mg/L of phytonadione as vitamin K, 0.4 to 30.0 mg/L of thiamine hydrochloride as vitamin $B_1$, 0.5 to 6.0 mg/L of riboflavin as vitamin $B_2$, 0.5 to 8.0 mg/L of pyridoxine hydrochloride as vitamin $B_6$, 0.5 to 50.0 µg/L of cyanocobalamin as vitamin $B_{12}$, 5.0 to 80.0 mg/L of nicotinamide as a nicotinic compound, 1.5 to 35.0 mg/L of pantothenic acid as a pantothenic compound, 50 to 800 µg/L of folic acid, 12 to 200 mg/L of ascorbic acid as vitamin C, 5 to 120 µg/L of biotin, 10 to 160 mEq/L of sodium ions, 1 to 40 mEq/L of magnesium ions, 5 to 80 mEq/L of potassium ions, 1 to 40 mEq/L of calcium ions, 10 to 160 mEq/L of chloride ions, 0 to 5 mEq/L of iodide ions, and 1 to 40 mmol/L of phosphate ions.

Effects of the Invention

According to the present invention, the dissolved oxygen content of the reduced-dissolved-oxygen-content drug solution can be maintained at a very low level. Therefore, it is possible to suppress the oxidative degradation of the drug solution and keep the drug solution highly stable over time.

The production method for the reduced-dissolved-oxygen-content drug solution according to the present invention permits efficient production of the drug solution having a dissolved oxygen content which is reduced to a very low level and maintained at the very low level for a long period of time. This makes it possible to suppress the oxidative degradation of the drug solution filled and sealed in the drug solution container for a long period of time and to maintain the drug solution highly stable over time.

In the reduced-dissolved-oxygen-content drug solution containing pack according to the present invention, the dissolved oxygen content of the drug solution can be maintained at a very low level. Therefore, the drug solution containing pack is capable of suppressing the oxidative degradation of the drug solution for a long period of time, and is highly stable over time.

DESCRIPTION OF REFERENCE CHARACTERS

Figure 1:
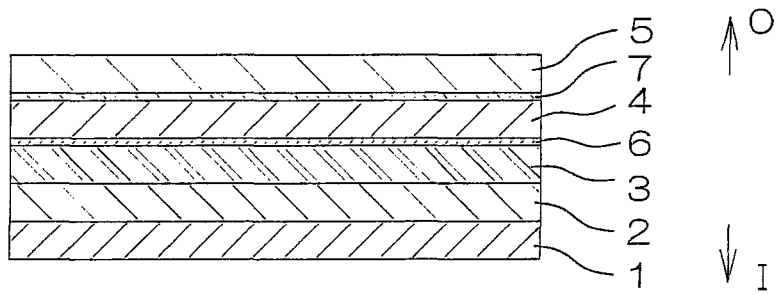
FIG. 1 is a schematic sectional view illustrating an exemplary plastic material to be employed for formation of a drug solution container.

10: Drug solution container, 12: Container portion, 15: Drug solution container, 18: Removable partition (Weakly sealed portion), 19: First container portion, 20: Second container portion, 21: Small bag, 22: Removable partition (Weakly sealed peripheral portion), 24: Removable partition (Weakly sealed portion), 25: Compartment, 26: Compartment Embodiments of the Invention An inventive drug solution with a reduced dissolved oxygen content is characterized in that the drug solution is contained and sealed in a drug solution container formed of a plastic material having an oxygen permeability of not lower than 200 $cm^3/m^2 \cdot 24$ h·atm at a temperature of 25° C. at a humidity of 60% RH within 12 hours after a steam sterilization process or a hot water sterilization process and having a steady-state oxygen permeability of not higher than 100 $cm^3/m^2 \cdot 24$ h·atm at a temperature of 25° C. at a humidity of 60% RH, that the drug solution has been subjected to the steam sterilization process or the hot water sterilization process, and that the drug solution has a dissolved oxygen concentration of not higher than 2 ppm when the oxygen permeability of the plastic material reaches the steady-state level after the steam sterilization process or the hot water sterilization process.

Any of various types of drug solutions may be contained and sealed as the inventive reduced-dissolved-oxygen-content drug solution in the drug solution container. Particularly, a drug solution containing an easily oxidizable drug (oxidation-prone drug) is preferred. The drug solution container which contains the reduced-dissolved-oxygen-content drug solution is capable of preventing intrusion of oxygen therein from the outside. Therefore, even if the drug solution contains the oxidation-prone drug, the drug solution contained in the drug solution container can be stably stored over time.

The oxidation-prone drug may be any of various types of drugs containing oxidation-prone components. Examples of the oxidation-prone components include amino acids and vitamins.

Examples of the amino acids include so-called essential amino acids and other amino acids, and salts, esters and N-acylated compounds of these amino acids. Specific examples of the amino acids include L-leucine, L-isoleucine, L-valine, L-lysine, L-threonine, L-tryptophan, L-methionine, L-cysteine, L-phenylalanine, L-tyrosine, L-arginine, L-histidine, L-alanine, L-proline, L-serine, L-glycine, L-aspartic acid and L-glutamic acid. These amino acids may be in the form of inorganic acid salts such as L-arginine hydrochloride, L-cysteine hydrochloride, L-glutamic hydrochloride, L-histidine hydrochloride and L-lysine hydrochloride, organic acid salts such as L-lysine acetate and L-lysine malate, esters such as L-tyrosine methyl ester, L-methionine methyl ester and L-methionine ethyl ester, N-substituted compounds such as N-acetyl-L-cysteine, N-acetyl-L-tryptophan and N-acetyl-L-proline, and dipeptides such as L-tyrosyl-L-tyrosine, L-alanyl-L-tyrosine, L-arginyl-L-tyrosine and L-tyrosyl-L-arginine. These amino acids may be contained either alone or in combination in the drug solution.

The vitamin may be any of various types of vitamins. Specific examples of the vitamins include lipid-soluble vitamins such as vitamin A, vitamin D, vitamin E and vitamin K, and water-soluble vitamins such as vitamin $B_1$, vitamin $B_2$, vitamin $B_6$, vitamin $B_{12}$, vitamin C, folic acid, niacin (nicotinic compounds), biotin (vitamin H) and pantothenic compounds.

Examples of vitamin A include retinol, retinal, retinoic acid, and esters of retinol (e.g., retinol palmitate and retinol acetate), among which retinol palmitate is preferred. Examples of vitamin D include vitamin $D_1$, vitamin $D_2$ (ergocalciferol) and vitamin $D_3$ (cholecalciferol), and active forms (hydroxyl derivatives) of these compounds, among which cholecalciferol is preferred. Examples of vitamin E include a-tocopherol, β-tocopherol, γ-tocopherol, d-tocopherol, a-tocotrienol, β-tocotrienol, γ-tocotrienol and d-tocotrienol, and esters of these compounds (e.g., acetates and succinates of these compounds), among which tocopherol acetate is preferred. Examples of vitamin K include vitamin $K_1$ (phylloquinone or phytonadione (generic name)), vitamin $K_2$ (menaquinone) and vitamin $K_3$ (menadione), among which phytonadione is preferred.

Examples of vitamin $B_1$ include thiamine and thiamine derivatives (e.g., thiamine hydrochloride, prosultiamine and octothiamine), among which thiamine hydrochloride is preferred. Examples of vitamin $B_2$ include riboflavin, riboflavin phosphate (phosphoric ester of riboflavin) and its sodium salt, flavin mononucleotide and flavin adenine dinucleotide, among which riboflavin phosphate is preferred. Examples of vitamin $B_6$ include pyridoxal, pyridoxine, pyridoxamine and pyridoxine hydrochloride, among which pyridoxine hydrochloride is preferred. An example of vitamin $B_{12}$ is cyanocobalamin. Examples of vitamin C include ascorbic acid and sodium ascorbate, among which ascorbic acid is preferred. Examples of niacin include nicotinic acid and nicotinamide. Examples of the pantothenic compounds include pantothenic acid, a calcium salt of pantothenic acid and panthenol obtained by reduction of pantothenic acid, among which panthenol is preferred. Examples of vitamin P include flavonoids.

The aforementioned vitamins may be contained either alone or in combination in the drug solution. The water-soluble vitamins may be used either alone or in combination to be blended with an amino acid containing drug solution or a saccharide containing drug solution.

Specific examples of the drug solution containing the oxidation-prone drug include an amino acid containing solution, a saccharide solution which contains vitamins (vitamin containing saccharide solution), and a lipid-soluble vitamin containing solution.

The amino acid containing solution may be a drug solution which contains the aforementioned exemplary amino acids either alone or in combination. The amino acid containing solution may further contain, for example, an electrolyte and a water-soluble vitamin as optional components.

Examples of the water-soluble vitamin to be contained in the amino acid containing solution include the aforementioned exemplary water-soluble vitamins, among which nicotinamide and folic acid are preferred. These water-soluble vitamins may be contained either alone or in combination in the amino acid containing solution. These water-soluble vitamins can stably coexist with the amino acid.

Examples of the electrolyte to be contained in the amino acid containing solution include water-soluble salts that supply ions such as sodium ions ($Na^+$), magnesium ions ($Mg^{2+}$), potassium ions ($K^+$), calcium ions ($Ca^{2+}$), chloride ions ($Cl^-$), iodide ions ($I^-$), phosphate ions (more specifically, hydrogen phosphate ions ($HPO_4^{2-}$), or dihydrogen phosphate ions ($H_2PO_4^-$)) and glycerophosphate ions ($C_3H_7O_3PO_3^{2-}$). These electrolytes can stably coexist with the amino acid.

Examples of a water-soluble salt as a sodium ion supply source include sodium chloride, sodium acetate, sodium citrate, sodium lactate, sodium dihydrogen phosphate, disodium hydrogen phosphate, sodium glycerophosphate and sodium sulfate. Examples of a water-soluble salt as a magnesium ion supply source include magnesium sulfate, magnesium chloride and magnesium acetate, among which magnesium sulfate is preferred. Examples of a water-soluble salt as a potassium ion supply source include potassium chloride, potassium iodide, potassium acetate, potassium citrate, potassium dihydrogen phosphate, dipotassium hydrogen phosphate, potassium glycerophosphate, potassium sulfate and potassium lactate, among which potassium acetate is preferred. Examples of a water-soluble salt as a calcium ion supply source include calcium chloride, calcium gluconate, calcium pantothenate, calcium lactate and calcium acetate, among which calcium chloride is preferred.

Examples of a water-soluble salt as a chloride ion supply source include sodium chloride, potassium chloride and calcium chloride, among which calcium chloride is preferred. Examples of a water-soluble salt as an iodide ion supply source include sodium iodide, magnesium iodide, potassium iodide and calcium iodide. Examples of a water-soluble salt as a phosphate ion supply source include sodium dihydrogen phosphate, disodium hydrogen phosphate, magnesium hydrogen phosphate, magnesium dihydrogen phosphate, potassium dihydrogen phosphate, dipotassium hydrogen phosphate, calcium hydrogen phosphate and calcium dihydrogen phosphate. Examples of a water-soluble salt as a glycerophosphate ion supply source include sodium glycerophosphate, potassium glycerophosphate and calcium glycerophosphate.

It is not preferred that the water-soluble calcium ion containing salt and the water-soluble phosphate ion containing salt coexist as electrolytes in the amino acid containing solution. Where calcium ions and phosphate ions are simultaneously administered, it is preferred that a multi-chamber container having two or more container portions is used as the drug solution container, and at least one of the water-soluble calcium ion containing salt and the water-soluble phosphate ion containing salt is contained in a container portion in which the amino acid containing solution is absent.

The amino acid containing solution may further contain, for example, an antioxidant and a pH adjusting agent. An example of the antioxidant is sodium hydrogen sulfite.

Examples of the pH adjusting agent include acids such as hydrochloric acid, acetic acid, lactic acid, malic acid, succinic acid and citric acid, and alkalis such as sodium hydroxide and potassium hydroxide. Any of these acids and alkalis each serving as the pH adjusting agent may be blended in the form of a water-soluble salt thereof as the electrolyte ion supply source in the amino acid containing solution.

The pH of the amino acid containing solution is preferably adjusted at 2.5 to 10, more preferably 5 to 8, for example, by properly using the pH adjusting agent.

Where the amino acid containing solution is stored in the form of a mixture with a saccharide solution, the stability of the mixture is liable to be deteriorated over time. Therefore, where the amino acid containing solution and the saccharide solution are simultaneously administered, it is preferred that a multi-chamber container having two or more container portions is used, and the amino acid containing solution and the saccharide solution are separately contained in the container.

An example of the vitamin containing saccharide solution is a drug solution containing a saccharide and a water-soluble vitamin.

The saccharide to be contained in the vitamin containing saccharide solution is not particularly limited, but any of saccharides conventionally used for various types of infusion solutions may be used. Examples of the saccharides include monosaccharides such as glucose, fructose and galactose, disaccharides such as maltose, lactose and sucrose, among which glucose is preferred. These saccharides may be used either alone or in combination.

Examples of the water-soluble vitamin to be contained in the vitamin containing saccharide solution include the aforementioned exemplary water-soluble vitamins, which may be contained either alone or in combination in the solution. These water-soluble vitamins each stably coexist with the saccharide solution.

The vitamin containing saccharide solution may contain an electrolyte as an optional component.

Examples of the electrolyte to be contained in the vitamin containing saccharide solution include water-soluble salts capable of supplying ions such as sodium ions, magnesium ions, potassium ions, calcium ions, chloride ions, iodide ions, phosphate ions, glycerophosphate ions. These electrolytes may be contained either alone or in combination in the solution. These electrolytes each stably coexist with the saccharide solution.

Examples of a water-soluble salt as a sodium ion supply source include those to be contained in the amino acid containing solution, among which sodium chloride and sodium lactate are preferred. Examples of a water-soluble salt as a magnesium ion supply source include those to be contained in the amino acid containing solution. Examples of a water-soluble salt as a potassium supply source include those to be contained in the amino acid containing solution, among which potassium chloride, potassium iodide and potassium dihydrogen phosphate are preferred. Examples of a water-soluble salt as a calcium ion supply source include those to be contained in the amino acid containing solution.

Examples of a water-soluble salt as a chloride ion supply source include those to be contained in the amino acid containing solution, among which sodium chloride and potassium chloride are preferred. Examples of a water-soluble salt as an iodide ion supply source include those to be contained in the amino acid containing solution, among which potassium iodide is preferred. Examples of a water-soluble salt as a phosphate ion supply source include those to be contained in the amino acid containing solution, among which potassium dihydrogen phosphate is preferred. Examples of a water-soluble salt as a glycerophosphate ion supply source include those to be contained in the amino acid containing solution.

The vitamin containing saccharide solution may further contain, for example, a pH adjusting agent, a saccharide alcohol and glycerin.

Examples of the pH adjusting agent include those described above. Any of these acids and alkalis each serving as the pH adjusting agent may be blended in the form of a water-soluble salt thereof as the electrolyte ion supply source in the vitamin containing saccharide solution.

Examples of the saccharide alcohol include sorbitol, xylitol, maltitol, paratinit, lactitol and erythritol.

The pH of the vitamin containing saccharide solution is preferably adjusted at 2 to 6, more preferably 2.5 to 5, for example, by properly using the pH adjusting agent.

Although the vitamin containing saccharide solution is employed as the drug solution containing the oxidation-prone drug by way of example in the above description, it is not essential to mix the saccharide with the vitamin. For example, the drug solution may contain the saccharide alone, or may contain the saccharide and the electrolyte.

The saccharide containing solution (saccharide solution) is liable to become unstable over time if being stored in the form of a mixture with the amino acid containing solution. Therefore, where the saccharide and the amino acid containing solution are simultaneously administered, for example, a multi-chamber container having two or more container portions is used as the drug solution container, and the saccharide and the amino acid containing solution are separately contained in the container.

The lipid-soluble vitamin containing solution contains the aforementioned exemplary lipid-soluble vitamins either alone or in combination. The lipid-soluble vitamin containing solution may contain Vitamin $B_2$.

The lipid-soluble vitamin containing solution may contain a surfactant as an optional component for solubilizing the lipid-soluble vitamin in an aqueous medium. Where the lipid-soluble vitamin is contained together with the surfactant in the aqueous medium, a water-soluble vitamin may be further contained in the aqueous medium as required.

Examples of the surfactant include sorbitan esters of fatty acids (more specifically, polysorbate) which are nonionic surfactants.

Examples of the water-soluble vitamin include the aforementioned exemplary water-soluble vitamins.

The lipid-soluble vitamin is generally poor in dispersibility in the amino acid containing solution and the saccharide solution. In addition, where the lipid-soluble vitamin is stored in the form of a mixture with the amino acid containing solution or the saccharide solution, the mixture is liable to become unstable over time. Therefore, where the lipid-soluble vitamin containing solution and the amino acid containing solution or the saccharide solution are simultaneously administered, for example, a multi-chamber container including two or more container portions is used as the drug solution container, and the vitamin containing solution is contained separately from the amino acid containing solution or the saccharide solution in the container.

In a preferred embodiment of the inventive reduced-dissolved-oxygen-content drug solution, the amino acid containing solution, the vitamin containing saccharide solution and the lipid-soluble vitamin containing solution are separately contained in a multi-chamber container including at least three container portions.

In this embodiment, the amounts of the amino acid, the saccharide, the vitamin and the electrolyte are not particularly limited, but preferably fall within the following ranges based on the amount of the overall drug solution after the drugs in the respective container portions are mixed together for intravenous administration or the like. In the following, the amounts of the amino acids are each represented by a free amino acid equivalent.

Amino Acids
L-leucine: 0.4 to 20.0 g/L, preferably 0.8 to 10.0 g/L
L-isoleucine: 0.2 to 14.0 g/L, preferably 0.4 to 7.0 g/L
L-valine: 0.1 to 16.0 g/L, preferably 0.3 to 8.0 g/L
L-lysine: 0.2 to 14.0 g/L, preferably 0.5 to 7.0 g/L
L-threonine: 0.1 to 8.0 g/L, preferably 0.3 to 4.0 g/L
L-tryptophan: 0.04 to 3.0 g/L, preferably 0.08 to 1.5 g/L
L-methionine: 0.1 to 8.0 g/L, preferably 0.2 to 4.0 g/L
L-cysteine: 0.01 to 2.0 g/L, preferably 0.03 to 1.0 g/L
L-phenylalanine: 0.2 to 12.0 g/L, preferably 0.4 to 6.0 g/L
L-tyrosine: 0.01 to 2 g/L, preferably 0.02 to 1.0 g/L
L-arginine: 0.2 to 14.0 g/L, preferably 0.5 to 7.0 g/L
L-histidine: 0.1 to 8.0 g/L, preferably 0.3 to 4.0 g/L
L-alanine: 0.2 to 14.0 g/L, preferably 0.4 to 7.0 g/L
L-proline: 0.1 to 10.0 g/L, preferably 0.2 to 5.0 g/L
L-serine: 0.1 to 6.0 g/L, preferably 0.2 to 3.0 g/L
L-glycine: 0.1 to 12.0 g/L, preferably 0.3 to 6.0 g/L
L-aspartic acid: 0.01 to 4.0 g/L, preferably 0.03 to 2.0 g/L
L-glutamic acid: 0 to 6.0 g/L, preferably 0.1 to 3.0 g/L
Saccharide
Glucose: 20 to 800 g/L, preferably 50 to 400 g/L
Vitamins
Vitamin A: 400 to 6500 IU/L, preferably 800 to 6500 IU/L, more preferably about 800 to about 4000 IU/L
Vitamin D: 0.5 to 10.0 µg/L, preferably 1.0 to 10.0 µg/L, more preferably 1.0 to 6.0 µg/L, in the form of cholecalciferol
Vitamin E: 1.0 to 20.0 mg/L, preferably 2.5 to 20.0 mg/L, more preferably 2.5 to 12.0 mg/L, in the form of tocopherol acetate
Vitamin K: 0.2 to 4.0 mg/L, preferably 0.5 to 4.0 mg/L, more preferably 0.5 to 2.5 mg/L, in the form of phytonadione
Vitamin $B_1$: 0.4 to 30.0 mg/L, preferably 0.8 to 30.0 mg/L, more preferably 1.0 to 5.0 mg/L, in the form of thiamine hydrochloride
Vitamin $B_2$: 0.5 to 6.0 mg/L, preferably 1.0 to 6.0 mg/L, more preferably 1.0 to 4.0 mg/L, in the form of riboflavin
Vitamin $B_6$: 0.5 to 8.0 mg/L, preferably 1.0 to 8.0 mg/L, more preferably 1.0 to 5.0 mg/L, in the form of pyridoxine hydrochloride
Vitamin $B_{12}$: 0.5 to 50.0 µg/L, preferably 1.0 to 20.0 µg/L, more preferably 1.0 to 10.0 µg/L, in the form of cyanocobalamin
Nicotinic compound: 5.0 to 80.0 mg/L, preferably 10.0 to 80.0 mg/L, more preferably 10.0 to 50.0 mg/L, in the form of nicotinamide
Pantothenic compound: 1.5 to 35.0 mg/L, preferably 3.0 to 30.0 mg/L, in the form of pantothenic acid
Folic acid: 50 to 800 µg/L, preferably 100 to 800 µg/L, more preferably 100 to 120 µg/L
Vitamin C: 12 to 200 mg/L, preferably 25 to 200 mg/L, more preferably 25 to 120 mg/L, in the form of ascorbic acid
Biotin: 5 to 120 µg/L, preferably 15 to 120 µg/L, more preferably 15 to 70 µg/L
Electrolytes
Sodium ions: 10 to 160 mEq/L, preferably 20 to 80 mEq/L
Magnesium ions: 1 to 40 mEq/L, preferably 2 to 20 mEq/L
Potassium ions: 5 to 80 mEq/L, preferably 10 to 40 mEq/L
Calcium ions: 1 to 40 mEq/L, preferably 2 to 20 mEq/L
Chloride ions: 10 to 160 mEq/L, preferably 20 to 80 mEq/L
Iodide ions: 0 to 5 mEq/L, preferably 0.2 to 5 mEq/L
Phosphate ions: 1 to 40 mmol/L, preferably 2 to 20 mmol/L In the present invention, a fat emulsion may be blended in the drug solution as required, and contained together with the drug solution in the drug solution container.

The fat emulsion may be any of various known fat emulsions. These fat emulsions may be contained either alone or in combination in the drug solution.

Exemplary fats and oils for the fat emulsion include those conventionally employed for the fat emulsion. Specific examples of the fats and oils include vegetable oils such as soy bean oil, cotton seed oil, safflower oil, corn oil, palm oil, Japanese basil oil and sesame seed oil, and a fish oil such as cod liver oil. These oils may be used either alone or in combination. Examples of a fat emulsifier to be used for preparation of the fat emulsion include emulsifiers conventionally employed for pharmaceutical preparations such as a fat emulsion. Specific examples of the emulsifier include egg phospholipid and soy bean phospholipid. These emulsifiers may be used either alone or in combination.

The drug solution container in which the reduced-dissolved-oxygen-content drug solution is contained and sealed is formed of a plastic material having an oxygen permeability of not lower than 200 $cm^3/m^2 \cdot 24$ h·atm at a temperature of 25° C. at a humidity of 60% RH within 12 hours after the steam sterilization process or the hot water sterilization process and having a steady-state oxygen permeability of not higher than 100 $cm^3/m^2 \cdot 24$ h·atm at a temperature of 25° C. at a humidity of 60% RH.

The drug solution container is preferably a container which is flexible or soft so as to be deformable according to the amount of the drug solution to be contained therein with the volume of its head space minimized, but this arrangement is not limitative.

The oxygen permeability of the plastic material for the drug solution container is not lower than 200 $cm^3/m^2 \cdot 24$ h·atm, preferably not lower than 500 $cm^3/m^2 \cdot 24$ h·atm, more preferably not lower than 700 $cm^3/m^2 \cdot 24$ h·atm, at a temperature of 25° C. at a humidity of 60% RH within 12 hours after the steam sterilization process or the hot water sterilization process.

If the oxygen permeability at a temperature of 25° C. at a humidity of 60% RH within 12 hours after the steam sterilization process or the hot water sterilization process is lower than the aforementioned range, it is difficult to remove oxygen dissolved in the drug solution or oxygen present in the head space of the drug solution container after the steam sterilization process or the hot water sterilization process, thereby diminishing the drug solution oxidation suppressing effect. The upper limit of the oxygen permeability after the steam sterilization process or the hot water sterilization process is not particularly limited, but generally about 1000 $cm^3/m^2 \cdot 24$ h·atm in consideration of the properties of the plastic material to be used for the production of the drug solution container.

Conditions for the steam sterilization process are, for example, such that the process temperature is 100 to 121° C., the process atmosphere is a water vapor saturated atmosphere, the process period is 10 to 60 minutes, and the process pressure is an ordinary pressure or a pressure of 4000 hPa or lower. Conditions for the hot water sterilization process are, for example, such that the process pressure is an ordinary pressure or an increased pressure, the temperature of the hot water is 100 to 120° C. and the process period is 10 to 60 minutes.

The steady-state oxygen permeability of the plastic material for the drug solution container is not higher than 100 $cm^3/m^2 \cdot 24$ h·atm, preferably not higher than 70 $cm^3/m^2 \cdot 24$ h·atm, more preferably not higher than 30 $cm^3/m^2 \cdot 24$ h·atm, further more preferably not higher than 10 $cm^3/m^2 \cdot 24$ h·atm, at a temperature of 25° C. at a humidity of 60% RH.

If the steady-state oxygen permeability at a temperature of 25° C. at a humidity of 60% RH is higher than the aforementioned range, it is impossible to suppress the penetration of oxygen into the drug solution container and hence the oxidation of the drug solution when the drug solution container is cooled after the steam sterilization process or the hot water sterilization process. The lower limit of the steady-state oxygen permeability is preferably zero, but generally about 5 $cm^3/m^2 \cdot 24$ h·atm, preferably about 1 $cm^3/m^2 \cdot 24$ h·atm, more preferably about 0.5 $cm^3/m^2 \cdot 24$ h·atm, in consideration of the properties of the plastic material to be used for the production of the drug solution container.

The "steady-state" oxygen permeability of the plastic material is such that the oxygen permeability is changed within ±5% per hour, preferably within ±3% per hour, as measured under predetermined conditions (at a temperature of 25° C. at a humidity of 60% RH) over time after the plastic material is subjected to the steam sterilization process or the hot water sterilization process (this definition is also applicable to the following description).

The oxygen permeability of the plastic material is measured as an oxygen gas transmission rate ($O_2$GTR) in conformity with Method B (Constant Pressure Method) of "Gas Permeability Testing Method for Plastic Film and Sheet" specified by JIS $K7126_{-1987}$ (this definition is also applicable to the following description). Exemplary oxygen permeability measurement apparatuses include an apparatus available under the trade name of OX-TRAN (registered trade mark) from MOCON, Inc., and an apparatus available under the trade name of OPT-5000 from LYSSY, Inc.

The oxygen permeability of the plastic material for the drug solution container can be set at a desired level by properly selecting the type and the thickness of the plastic material. Where the plastic material has a multilayer structure, the oxygen permeability can be set at a desired level by properly selecting the layered structure and the thicknesses of respective layers.

Examples of the plastic material which has an oxygen permeability falling within the aforementioned range at a temperature of 25° C. at a humidity of 60% RH within 12 hours after the steam sterilization process or the hot water sterilization process and a steady-state oxygen permeability falling within the aforementioned range at a temperature of 25° C. at a humidity of 60% RH include polyol resins, among which an ethylene-vinyl alcohol copolymer is particularly preferred.

The ethylene-vinyl alcohol copolymer preferably has an ethylene content of 10 to 45 mol %, more preferably 25 to 35 mol %. If the ethylene content of the ethylene-vinyl alcohol copolymer is less than the aforementioned range, there is a possibility that the oxygen permeability is not reduced when the resulting container is cooled after the steam sterilization process or the hot water sterilization process, or that the resulting container fails to have water resistance sufficient to bear the steam sterilization process and the hot water sterilization process. On the other hand, if the ethylene content of the ethylene-vinyl alcohol copolymer is greater than the aforementioned range, there is a possibility that the steady-state oxygen permeability is increased, making it impossible to suppress the penetration of oxygen into the drug solution container. In this case, the plastic material is liable to be whitened by the steam sterilization process or the hot water sterilization process to drastically reduce the transparency of the container.

For improvement of the heat resistance of the drug solution container, a polyamide resin such as nylon-6 and a phosphorus-containing antioxidant such as tris(2,4-di-t-butylphenyl)phosphite may be blended in the polyol resin. The amounts of the polyamide resin and the phosphorus-containing antioxidant to be blended may be determined so as not to influence the drug solution to be contained in the drug solution container.

In order to impart the drug solution container with basic properties, the plastic material for the drug solution container has a multilayer structure including an intermediate layer of the polyol resin, a seal layer (innermost layer) of a polyolefin resin provided on an inner side of the intermediate layer of the drug solution container, and a protective layer (outermost layer) provided on an outer side of the intermediate layer of the drug solution container.

The seal layer (innermost layer) has a fusion-bonding surface to be fusion-bonded in production of the drug solution container, and is disposed on an inner side of the drug solution container to be brought into direct contact with the drug solution. Therefore, a plastic material for the seal layer (innermost layer) should have proper heat-sealability (more specifically, heat-sealing conditions such as a heating temperature, a heating period and a pressure and, the sealing strength and the stability of, for example, a heat-seal portion over time) and ensure safety for the drug solution.

Specific examples of the plastic material for the seal layer (innermost layer) include polyolefin resins.

Examples of the polyolefin resins include polyethylenes (ethylene homopolymers), ethylene/a-olefin copolymers, polypropylenes (propylene homopolymers), propylene/a-olefin random copolymers and propylene/a-olefin block copolymers. Exemplary a-olefins for the ethylene/a-olefin copolymers include $C_3$ to $C_6$ a-olefins such as propylene, 1-butene, 1-pentene, 1-hexene and 4-methyl-1-pentene. Exemplary a-olefins for the propylene/a-olefin random copolymers and the propylene/a-olefin block copolymers include ethylene, and $C_4$ to $C_6$ a-olefins such as 1-butene, 1-pentene, 1-hexene and 4-methyl-1-pentene. These polyolefin resins may be used either alone or in combination.

Among the aforementioned exemplary polyolefin resins for the seal layer, polyethylenes, polypropylenes and mixtures of any of these resins are preferred.

For production of a bag-like drug solution container (so-called multi-chamber bag) including a plurality of container portions isolated from each other by an unsealable partition wall (unsealable seal portion), the seal layer is preferably composed of a resin mixture of a polyethylene and a polypropylene for easy formation of the unsealable seal portion.

The protective layer (outermost layer) is disposed on an outer side of the drug solution container. Therefore, a resin material for the protective layer (outermost layer) is properly selected, for example, so as to prevent the intermediate layer of the polyol resin from being influenced directly by moisture during the steam sterilization process or the hot water sterilization process and to impart the drug solution container with a desired strength according to the shape and the use purpose of the drug solution container.

The protective layer (outermost layer) or layers provided on the outer side of the intermediate layer of the multilayer film of the drug solution container should be imparted with a certain water vapor permeability to provide the effects of the present invention while preventing the intermediate layer of the polyol resin from being influenced directly by the moisture.

The protective layer (outermost layer) or the layers provided on the outer side of the intermediate layer of the multilayer film of the drug solution container preferably has a water vapor permeability of 1 to 50 g/m$^2$·24 h, more preferably 3 to 30 g/m$^2$·24 h, further more preferably 3 to 10 g/m$^2$·24 h, at a temperature of 25° C. at a humidity of 90% RH. The water vapor permeability is measured in conformity with Method A (Moisture Sensor Method) of "Water Vapor Transmission Rate Testing Method for Plastic Film and Sheet (Instrumental method)" specified by JIS K7129-1992.

Specific examples of the resin for the protective layer (outermost layer) include polyolefin resins, polyamide resins and polyester resins. Examples of the polyolefin resins include the aforementioned exemplary polyolefins. Examples of the polyamide resins include nylons such as nylon-6, nylon-6,6 and nylon-6,10. Examples of the polyester resins include polyethylene terephthalates and polybutylene terephthalates.

Where the plastic material for the drug solution container is the multilayer film, the multilayer film has a layered structure including at least three layers, more specifically, the seal layer of the polyolefin resin provided as the innermost layer exposed in an inner surface of the drug solution container, the protective layer provided as the outermost layer exposed in an outer surface of the drug solution container, and the intermediate layer of the polyol resin provided between the seal layer and the protective layer as described above.

The multilayer film preferably further includes a less water-absorptive layer of a less water-absorptive resin provided on the inner side (seal layer side) of the intermediate layer of the drug solution container. In this case, the intermediate layer of the polyol resin is unlikely to be influenced by water in the drug solution.

Examples of the less water-absorptive resin include polycycloolefins.

The polycycloolefins each have a very low water absorbability, more specifically, a water absorbability of 0.01% or lower. Therefore, the polycycloolefins are advantageous for reducing the influence of the water exerted on the intermediate layer of the polyol resin. The water absorbability is measured in conformity with Method B (Water Absorption after Immersion in Boiling Water) of "Plastics—Determination of Water Absorption" specified by JIS K7209-2000.

Specific examples of the polycycloolefins include copolymers of ethylene and dicyclopentadiene compounds (and their hydrogenated products), copolymers of ethylene and norbornene compounds (and their hydrogenated products), ring-opening polymers of cyclopentadiene compounds (and their hydrogenated products), and ring-opening polymers of two or more types of cyclopentadiene compounds (and their hydrogenated products), among which the hydrogenated products of the copolymers of ethylene and the norbornene compounds and the hydrogenated products of the ring-opening (co)polymers of one or more types of cyclopentadiene derivatives. These polycycloolefins may be used either alone or in combination.

The multilayer film may further include an elastomer layer which contains an elastomer for imparting the drug solution container with flexibility, transparency and impact resistance.

Examples of the elastomer include polyolefin elastomers such as polyethylene elastomers and polypropylene elastomers, and styrene elastomers such as styrene-ethylene/butylene-styrene block copolymers (SEBS), styrene-butadiene-styrene block copolymers (SBS), styrene-isoprene-styrene block copolymer (SIS), SEBSs modified with maleic acid, styrene-ethylene/propylene-styrene block copolymers (SEPS), styrene-ethylene/butylene block copolymers (SEB) and styrene-ethylene/propylene block copolymers (SEP), among which the polyethylene elastomers are preferred.

The plastic material for the drug solution container is formed into a film, for example, by an extrusion method such as a T-die method or an inflation method, but the film formation method is not limited to this method. The drug solution container is produced from the film thus formed and, therefore, is highly flexible and soft.

The following multilayer films (I) to (III) are preferred examples of the multilayer film for the drug solution container.

(I) A multilayer film having a seven-layer structure including a seal layer 1 of a resin mixture of a polyethylene and a polypropylene, a layer 2 of a polyethylene, a less water-absorptive layer 3 of a polycycloolefin, an intermediate layer 4 of an ethylene-vinyl alcohol copolymer and a protective layer 5 of a polyethylene which are provided in this order from an inner side (innermost layer) I to an outer side (outermost layer) O of the drug solution container, and two adhesive layers 6, 7 of an adhesive resin provided between the less water-absorptive layer 3 and the intermediate layer 4 and between the intermediate layer 4 and the protective layer 5 (see FIG. 1).

Figure 2:
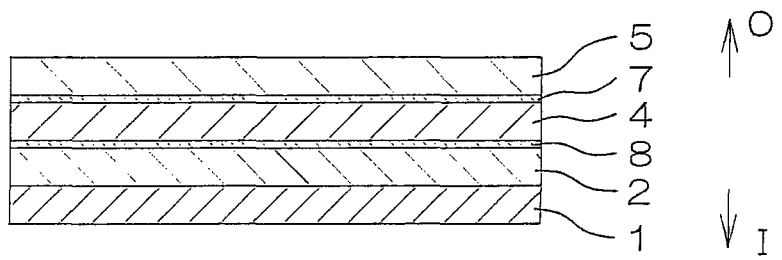
FIG. 2 is a schematic sectional view illustrating another exemplary plastic material to be employed for formation of a drug solution container.

(II) A multilayer film having a six-layer structure including a seal layer 1 of a resin mixture of a polyethylene and a polypropylene, a layer 2 of a polyethylene, an intermediate layer 4 of an ethylene-vinyl alcohol copolymer and a protective layer 5 of a polyethylene which are provided in this order from an inner side (innermost layer) I to an outer side (outermost layer) O of the drug solution container, and two adhesive layers 8, 7 of an adhesive resin provided between the polyethylene layer 2 and the intermediate layer 4 and between the intermediate layer 4 and the protective layer 5 (see FIG. 2).

Figure 3:
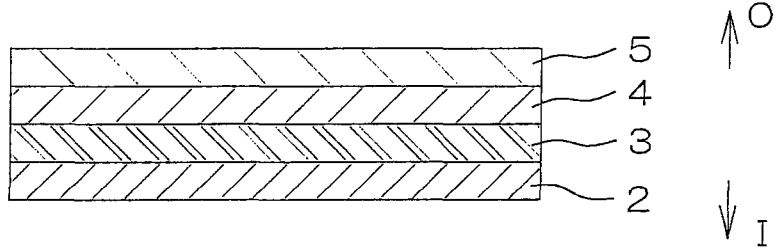
FIG. 3 is a schematic sectional view illustrating further another exemplary plastic material to be employed for formation of a drug solution container.

(III) A multilayer film having a four-layer structure including a layer 2 of a polyethylene, a less water-absorptive layer 3 of a polycycloolefin, an intermediate layer 4 of an ethylene-vinyl alcohol copolymer and a protective layer 5 of a polyethylene which are provided in this order from an inner side (innermost layer) I to an outer side (outermost layer) O of the drug solution container (see FIG. 3).

In the multilayer films (I) and (II), the bonding between the less water-absorptive layer 3 and the intermediate layer 4 and the bonding between the intermediate layer 4 and the protective layer 5 are achieved by the provision of the two adhesive layers 6 and 7, respectively. Alternatively, the bonding between the layers may be achieved by applying an adhesive agent between the layers without the provision of the adhesive layers.

In the multilayer film (III), the bonding between the less water-absorptive layer 3 and the intermediate layer 4 and the bonding between the intermediate layer 4 and the protective layer 5 are achieved by applying an adhesive agent between these layers. As in the case of the multilayer films (I) and (II), the bonding between the layers may be achieved by the provision of the adhesive layers. In the multilayer film (III), the polyethylene layer 2 is an innermost layer, which serves as a seal layer.

Examples of the adhesive resin for the adhesive layers include adhesive polyolefins. Specific examples of the adhesive resin include adhesive polyols available under the trade name of ADMER (registered trade mark) series from Mitsui Chemicals, Inc.

Examples of the adhesive agent include polyurethane resins. Specific examples of the adhesive agent include polyurethane resins available under the trade names of TAKERACK (registered trade mark) series and TAKENATE (registered trade mark) series from Mitsui Chemicals Polyurethane, Inc.

The thicknesses of the respective layers of the multilayer films are not particularly limited, but may be set so that the oxygen permeability of the entire drug solution container after the steam sterilization process or the hot water sterilization process and the steady-state oxygen permeability of the entire drug solution container fall within the aforementioned ranges.

Where the drug solution container is a bag type container to be described later, it is preferred that the intermediate layer has a thickness of 3 to 20 μm and the multilayer film has an overall thickness of about 180 to about 300 μm, but this arrangement is not limitative.

The drug solution container may be, for example, of a so-called bag type which is flat and highly flexible and soft, or of a so-called bottle type which is flexible and has strength sufficient to maintain its container shape. Particularly, the drug solution container of the bag type is preferred.

The method of producing the drug solution container is not particularly limited, but may be properly selected according to the shape of the drug solution container.

For example, the drug solution container of the bag type may be a drug solution container including a single container portion for containing a drug solution, or a so-called multi-chamber container including a plurality of container portions isolated from each other by a weakly sealed portion.

Figure 4:
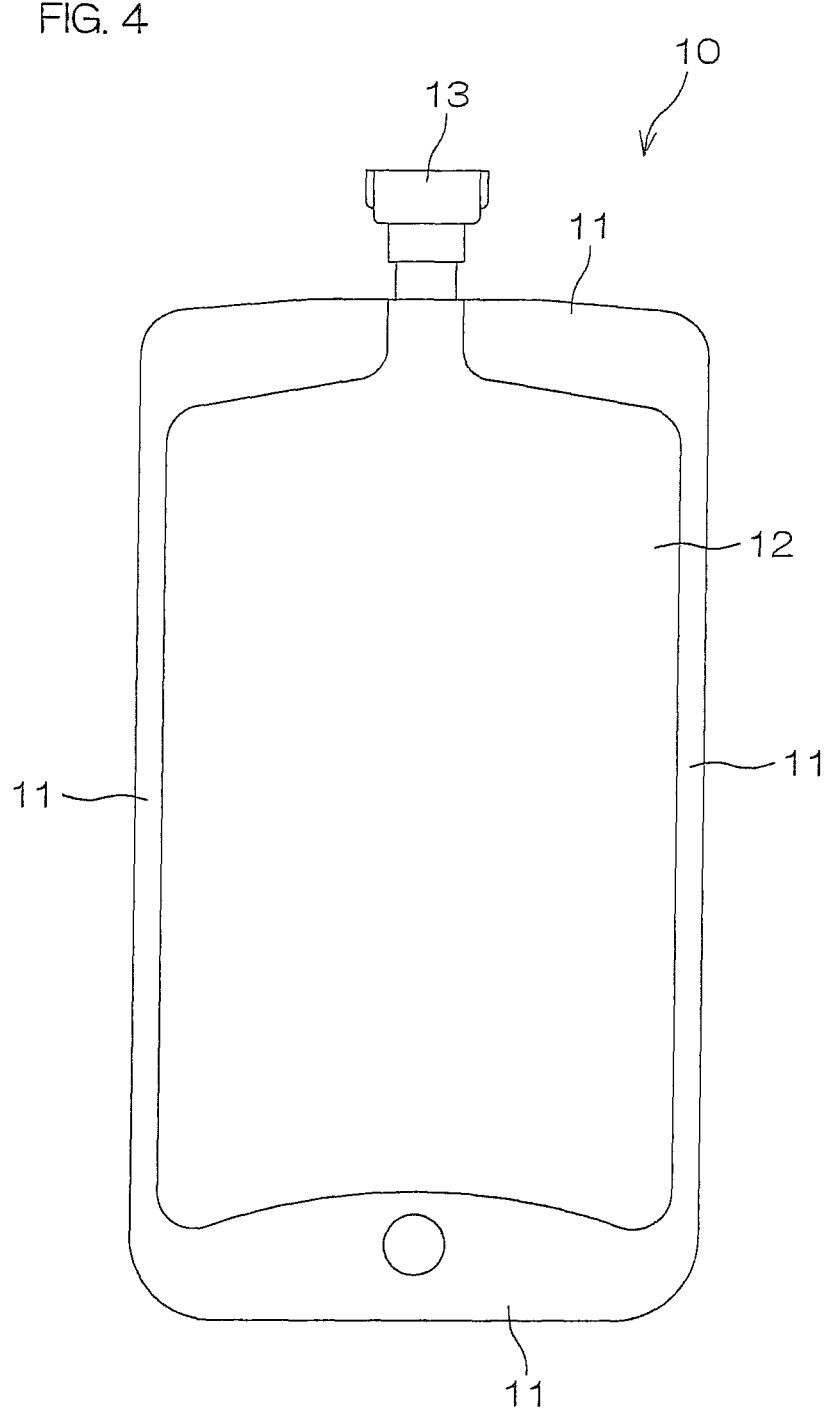
FIG. 4 is a front view illustrating an exemplary drug solution container.
Figure 5:
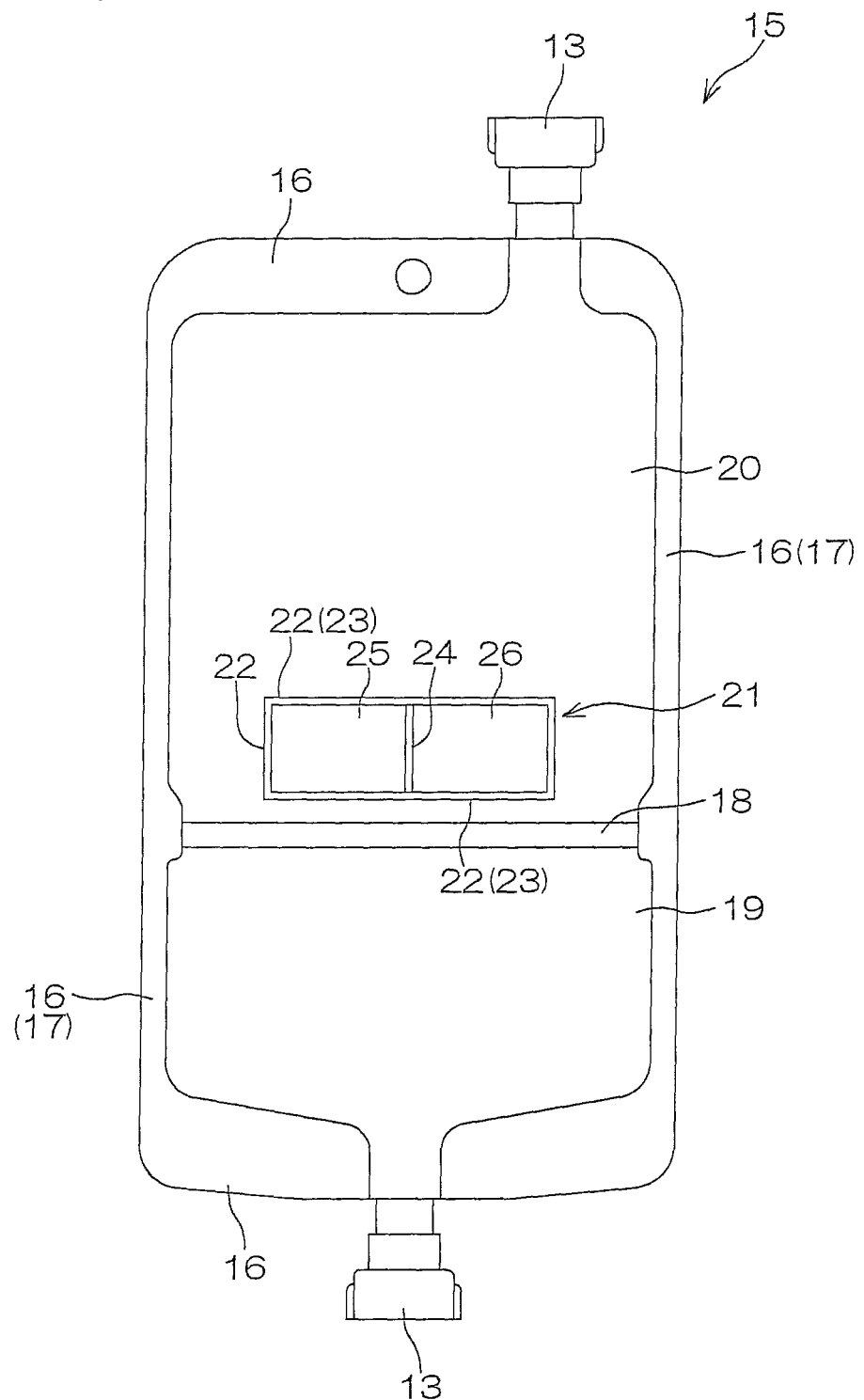
FIG. 5 is a front view illustrating another exemplary drug solution container.

Bag-type drug solution containers are shown as preferred examples of the drug solution container in FIGS. 4 and 5.

Referring to FIG. 4, a bag-type drug solution container 10 includes a heavily sealed peripheral portion 11 which is formed by heat-sealing peripheral edge portions of two plastic films (a front film and a rear film) stacked one on the other, and a container portion 12 defined by the heavily sealed peripheral portion 11 for containing a drug solution. A tube member 13 which permits communication between the container portion 12 and the outside of the drug solution container 10 is provided between the front film and the rear film at a part of the heavily sealed peripheral portion 11.

Referring to FIG. 5, a multi-chamber drug solution container 15 of the bag type includes a heavily sealed peripheral portion 16 which is formed by heavily heat-sealing peripheral edge portions of two plastic films (a front film and a rear film) stacked one on the other, and a container portion defined by the heavily sealed peripheral portion 16 for containing a drug solution. The heavily sealed peripheral portion 16 includes a pair of heavily sealed side portions 17 which are spaced from each other in a transverse direction perpendicular to the lengths of the two plastic films, and a weakly sealed portion 18 extends in the transverse direction between the heavily sealed side portions 17. The container portion is partitioned into a first container portion 19 disposed on a lower side as seen from the front side and a second container portion 20 disposed on an upper side as seen from the front side by the weakly sealed portion 18.

A small bag 21 having a generally rectangular front shape for containing a drug solution is provided in the second container portion 20. The small bag 21 includes a weakly sealed peripheral portion 22 which is formed by weakly heat-sealing peripheral edge portions of two plastic films (a front film and a rear film) stacked one on the other, and a container portion defined by the weakly sealed peripheral portion 22 for containing the drug solution. The container portion is partitioned into two compartments 25, 26, which are each defined by the weakly sealed peripheral portion 22 and a weakly sealed portion 24 extending between a pair of longer edges 23 of the weakly sealed peripheral portion 22. The front film and the rear film of the small bag 21 are respectively fixed to the front film and the rear film of the multi-chamber container 15.

The weakly sealed portion 18 provided between the first container portion 19 and the second container portion 20 is unsealed by pressing either of the two container portions 19, 20 to cause the drug solutions contained in the container portions 19, 20 to apply a liquid pressure to the weakly sealed portion 18. The weakly sealed peripheral portion 22 of the small bag 21 is also unsealed when the two container portions 19, 20 are caused to communicate with each other by the unsealing of the weakly sealed portion 18. Thus, the drug solutions separately contained in the first container portion 19, the second container portion 20 and the two compartments 25, 26 of the small bag 21 are mixed together.

The aforementioned plastic films or the multilayer films for the production of the drug solution container are employed as the two plastic films for the drug solution container shown in FIG. 4 and the two plastic films for the multi-chamber container 15 shown in FIG. 5.

The two plastic films for the formation of the small bag 21 of the multi-chamber container 15 shown in FIG. 5 are preferably formed of an oxygen-permeable plastic, but this arrangement is not limitative. Where the small bag 21 is formed of the oxygen-permeable plastic, oxygen can easily migrate between the small bag 21 and the second container portion 20. Therefore, the amount of oxygen dissolved in the drug solution contained in the small bag 21 can be reduced in the same manner as for the oxygen dissolved in the drug solutions contained in the two container portions 19, 20.

Examples of the oxygen-permeable plastic include polyolefins such as polyethylenes and polypropylenes, and polycycloolefins, which are safe and commonly used as materials for medical containers.

A drug solution container including a small bag provided in one of container portions, like the multi-chamber container 15 shown in FIG. 5, is well-known. Specific examples of such a drug solution container include a medical multi-chamber container disclosed in International Publication WO2003/092574, and a medical multi-chamber container disclosed in JP-T-2005-523772.

In the drug solution container having the small bag provided in the one container portion, like the multi-chamber container 15 shown in FIG. 5, the lipid-soluble vitamin containing solution is preferably contained in the small bag 21, but this arrangement is not limitative. Where the small bag is partitioned into two compartments, it is preferred that the lipid-soluble vitamin containing solution is contained in the one compartment 25 and the micronutrient metal element containing solution is contained in the other compartment 26, but this arrangement is not limitative.

As described above, the reduced-dissolved-oxygen-content drug solution is characterized in that the drug solution is filled and sealed in the drug solution container and then subjected to the steam sterilization process or the hot water sterilization process, and that the dissolved oxygen concentration thereof is not higher than 2 ppm when the oxygen permeability of the plastic material reaches the steady-state level after the steam sterilization process or the hot water sterilization process.

More specifically, an exemplary method for the steam sterilization process is a high pressure steam sterilization (autoclave) method. Exemplary methods for the hot water sterilization process include a hot water immersion sterilization method and a hot water shower sterilization method.

The drug solution container (drug solution containing pack) which contains the drug solution is heated for a predetermined period during the steam sterilization process or the hot water sterilization process. Therefore, the oxygen permeability of the plastic material for the drug solution container can be increased. More specifically, the oxygen permeability of the plastic material for the drug solution container is set at a level not lower than 200 cm$^3$/m$^2$·24 h·atm as measured at a temperature of 25° C. at a humidity of 60% RH within 12 hours after the steam sterilization process or the hot water sterilization process.

Conditions for the steam sterilization process or the hot water sterilization process to be preformed on the drug solution container are properly determined according to the type and the amount of the drug solution to be contained in the drug solution container and the material and the thickness of the plastic material for the drug solution container.

Therefore, the conditions for the steam sterilization process are not particularly limited, but may be determined as described above. For example, the conditions for the steam sterilization process are preferably such that the process temperature is 100 to 121° C., the process period is 10 to 60 minutes, and a process pressure is 2000 to 3500 hPa. Conditions for the hot water sterilization process may be determined as described above. In the hot water sterilization process, hot water is jetted or sprayed over the drug solution container.

The steam sterilization process or the hot water sterilization process is preferably performed in an inert gas atmosphere. In this case, gas present in the head space of the drug solution container can be replaced with an inert gas to some extent during the steam sterilization process or the hot water sterilization process, so that the amount of oxygen in the drug solution container or the amount of oxygen to be removed from the head space during the steam sterilization process or the hot water sterilization process can be preliminarily reduced.

The inert gas is not particularly limited, but examples of the inert gas include nitrogen and argon, which are less liable to (preferably do not) cause oxidative decomposition or degradation of the drug solution.

After the drug solution container (drug solution containing pack) which contains the drug solution is subjected to the steam sterilization process or the hot water sterilization process, the drug solution container containing the drug solution is stored in an environment having deoxidation means until the oxygen permeability of the plastic material for the drug solution container reaches the steady-state level. Thus, the dissolved oxygen concentration of the drug solution can be adjusted at not higher than 2 ppm when the oxygen permeability of the plastic material for the drug solution container reaches the steady-state level.

The dissolved oxygen concentration of the drug solution is not higher than 2 ppm when the oxygen permeability of the plastic material reaches the steady-state level after the steam sterilization process or the hot water sterilization process.

After the steam sterilization process or the hot water sterilization process, a period required for the oxygen permeability of the plastic material for the drug solution container to reach the steady-state level is typically 7 days, preferably 10 days, more preferably 14 days. In order to reduce the amount of the oxygen dissolved in the drug solution contained in the drug solution container and the amount of the oxygen present in the head space of the drug solution container, it is preferred that the drug solution container is stored in the environment having the deoxidation means for the aforementioned period after the steam sterilization process or the hot water sterilization process.

The deoxidation means reacts with oxygen or absorbs oxygen to reduce the oxygen content in the hermetic environment. A specific example of the deoxidation means is an oxygen scavenger.

Any of various known oxygen scavengers may be used, but specific examples of the oxygen scavenger include oxygen scavengers containing an iron compound such as iron hydroxide, iron oxide or iron carbide as an active component, and oxygen scavengers containing a lower molecular weight phenol and an active carbon as active components. Examples of a commercially available oxygen scavenger include AGELESS (registered trade mark) available from Mitsubishi Gas Chemical Company Inc., MODURAN (trade name) available from Nippon Kayaku Co., Ltd., SEQUL (registered trade mark) available from Nippon Soda Co., Ltd., TAMOTSU (registered trade mark) available from Oji Kako Co., Ltd., BITARON (trade name) available from Toagosei Co., Ltd., SANSOCUT (trade name) available from FINETECH Inc., and OXYGUARD (trade name) available from Toyo Seikan Kaisha, Ltd.

A process for reducing the dissolved oxygen content of the drug solution by the deoxidation means is preferably performed in a hermetic environment defined by an outer package having an oxygen barrier property.

An aluminum laminate film or the like may be used as the outer package having the oxygen barrier property.

An inventive production method for the reduced-dissolved-oxygen-content drug solution includes: a drug solution filling step of filling and sealing a drug solution in a drug solution container formed of a plastic material having an oxygen permeability of not lower than 200 cm$^3$/m$^2$·24 h·atm at a temperature of 25° C. at a humidity of 60% RH within 12 hours after a steam sterilization processor a hot water sterilization process and having a steady-state oxygen permeability of not higher than 100 cm$^3$/m$^2$·24 h·atm at a temperature of 25° C. at a humidity of 60% RH; a sterilization step of subjecting the drug solution container to the steam sterilization process or the hot water sterilization process after the drug solution filling step; and a dissolved oxygen content reducing step of reducing the dissolved oxygen concentration of the drug solution to not higher than 2 ppm by storing the drug solution container in an environment having deoxidization means until the oxygen permeability of the plastic material reaches the steady-state level after the sterilization step.

The drug solution container is the same as the drug solution container in which the inventive reduced-dissolved-oxygen-content drug solution is contained and sealed. More specifically, the drug solution container is provided in the same form by the same production method as described above. Further, the properties (particularly, the oxygen permeability after the steam sterilization process or the hot water sterilization process, and the steady-state oxygen permeability), the materials and the layered structure of the plastic material or the multilayer film for the drug solution container are the same as those described above. Since the drug solution container has a very high oxygen permeability for a predetermined period after the steam sterilization process or the hot water sterilization process, the amount of the oxygen dissolved in the drug solution and the amount of the oxygen remaining in the drug solution container can be reduced outside the drug solution container. Further, the steady-state oxygen permeability is very low, so that the intrusion of oxygen from the outside can be significantly suppressed. Therefore, the drug solution container can stably contain and store, for example, an oxidation-prone drug over time.

Various drug solutions may be filled and sealed in the drug solution container. Particularly, the drug solution preferably contains the oxidation-prone drug. Examples of the drug solution to be filled and sealed in the drug solution container include those of the aforementioned reduced-dissolved-oxygen-content drug solution to be contained and sealed in the drug solution container. Specific examples of the oxidation-prone drug (amino acids, vitamins and the like), and the ingredients and the formulations of an amino acid containing solution, a vitamin containing saccharide solution, a lipid-soluble vitamin containing solution and the like are the same as those described above.

The method of filling the drug solution in the drug solution container in the drug solution filling step is not particularly limited. The drug solution may be filled in the drug solution container by an ordinary method.

In the sterilization step, the drug solution container is subjected to the steam sterilization process or the hot water sterilization process after the drug solution filling step. More specifically, an exemplary method for the steam sterilization process is a high pressure steam sterilization (autoclave) method. Further, exemplary methods for the hot water sterilization process include a hot water immersion sterilization method and a hot water shower sterilization method.

Conditions for the steam sterilization process or the hot water sterilization process to be performed on the drug solution container, and an inert gas to be used for the sterilization process are the same as those described above.

In the dissolved oxygen content reducing step, the dissolved oxygen concentration of the drug solution is reduced to a level not higher than 2 ppm by cooling the drug solution container in a hermetic environment having deoxidation means until the oxygen permeability of the plastic material reaches the steady-state level. In the dissolved oxygen content reducing step, the drug solution container which contains the drug solution is stored in the environment having the deoxidization means until the oxygen permeability of the plastic material for the drug solution container reaches the steady-state level after the steam sterilization process or the hot water sterilization process, whereby the dissolved oxygen concentration of the drug solution is adjusted at 2 ppm or lower when the oxygen permeability of the plastic material for the drug solution container reaches the steady-state level.

The method for the storage after the steam sterilization process or the hot water sterilization process, the deoxidation means and the method for the reduction of the dissolved oxygen content with the deoxidation means are the same as those described above.

The reduced-dissolved-oxygen-content drug solution and the production method for the drug solution can reduce the amount of the oxygen dissolved in the drug solution contained in the drug solution container and the amount of the oxygen present in the head space of the drug solution container, thereby suppressing the oxidative degradation of the drug solution. Therefore, the reduced-dissolved-oxygen-content drug solution and the production method for the drug solution are advantageous for stabilizing the oxidation-prone drug solution such as the amino acid containing solution, the vitamin containing saccharide solution, the lipid-soluble vitamin containing solution or the fat emulsion for a long period of time.

In an inventive drug solution containing pack with a reduced dissolved oxygen content, the drug solution container for containing the drug solution is formed of a plastic material having an oxygen permeability of not lower than 200 $cm^3/m^2 \cdot 24$ h·atm at a temperature of 25° C. at a humidity of 60% RH within 12 hours after the steam sterilization process or the hot water sterilization process and having a steady-state oxygen permeability of not higher than 100 $cm^3/m^2 \cdot 24$ h·atm at a temperature of 25° C. at a humidity of 60% RH.

The aforementioned drug solution container is the same as the drug solution container for containing and sealing the reduced-dissolved-oxygen-content drug solution of the invention. More specifically, the drug solution container is provided in the same form by the same production method as described above. Further, the properties (particularly, the oxygen permeability after the steam sterilization process or the hot water sterilization process, and the steady-state oxygen permeability), the materials and the layered structure of the plastic material or the multilayer film for the drug solution container are the same as those described above. Since the drug solution container has a very high oxygen permeability for a predetermined period after the steam sterilization process or the hot water sterilization process, the amount of oxygen dissolved in the drug solution and the amount of oxygen remaining in the drug solution container can be reduced outside the drug solution container. Further, the steady-state oxygen permeability is very low, so that the intrusion of oxygen from the outside can be significantly suppressed. Therefore, the drug solution container can stably contain and store, for example, an oxidation-prone drug over time.

Various drug solutions may be contained and sealed in the reduced-dissolved-oxygen-content drug solution containing pack. Particularly, the drug solution preferably contains the oxidation-prone drug. Examples of the drug solution to be contained and sealed in the drug solution container include those of the aforementioned reduced-dissolved-oxygen-content drug solution to be contained and sealed in the drug solution container. Specific examples of the oxidation-prone drug (amino acids, vitamins and the like), and the ingredients and the formulations of the amino acid containing solution, the vitamin containing saccharide solution, the lipid-soluble vitamin containing solution and the like are the same as those described above.

In the reduced-dissolved-oxygen-content drug solution containing pack, the drug solution container and the drug solution to be contained and sealed in the drug solution container are employed in the same combination as that of the drug solution container and the drug solution to be contained and sealed in the drug solution container of the aforementioned reduced-dissolved-oxygen-content drug solution.

In the drug solution containing pack, the drug solution may further contain a fat emulsion as required, and the fat emulsion may be contained together with the oxidation-prone drug solution in the drug solution container (e.g., the fat emulsion and the oxidation-prone drug solution may be separately contained in different container portions).

Any of various known fat emulsions is employed as the fat emulsion. The fat emulsions may be used either alone or in combination.

Exemplary fats and oils for the fat emulsion include those conventionally employed for the fat emulsion. Specific examples of the fats and oils include vegetable oils such as soy bean oil, cotton seed oil, safflower oil, corn oil, palm oil, Japanese basil oil and sesame seed oil, and fish oil such as cod liver oil. These oils may be used either alone or in combination. Exemplary emulsifiers for the fat emulsion include those conventionally employed for pharmaceutical preparations such as a fat emulsion. Specific examples of the emulsifiers include egg phospholipid and soy bean phospholipid. These emulsifiers may be used either alone or in combination.

In a preferred embodiment of the inventive reduced-dissolved-oxygen-content drug solution containing pack, the drug solution container includes a plurality of container portions isolated from each other by a removable partition. An amino acid containing solution is contained in one of the container portions, and a saccharide solution is contained in another one of the container portions.

The drug solution container including the plurality of container portions isolated from each other by the removable partition may be, for example, a bag type container as described above.

Examples of the amino acid containing solution to be contained in the one container portion include the aforementioned exemplary amino acid containing solutions, and examples of the saccharide solution to be contained in the another container portion include the aforementioned exemplary vitamin containing saccharide solutions, and saccharide solutions obtained by excluding vitamins from the vitamin containing saccharide solutions.

In another preferred embodiment of the inventive reduced-dissolved-oxygen-content drug solution containing pack, the drug solution container includes a plurality of container portions isolated from each other by a removable partition, and one of the container portions is a small bag provided in another one of the container portions. Further, the small bag is partitioned into two compartments. A lipid-soluble vitamin containing solution is contained in one of the two compartments, and a micronutrient metal element drug solution is contained in the other compartment.

Where the one container portion is the small bag provided in the another container portion, the small bag may be arranged in the aforementioned manner (see FIG. 5), but this arrangement is not limitative.

Examples of the lipid-soluble vitamin containing solution to be contained in the small bag include the aforementioned exemplary lipid-soluble vitamin containing solutions.

Examples of the micronutrient metal element drug solution to be contained in the small bag include drug solutions which contain a micronutrient metal element component including at least one element selected from the group consisting of iron, manganese, zinc, copper, selenium, molybdenum, cobalt and chromium.

The micronutrient metal element component includes metal elements that alleviate various deficiency symptoms occurring when a human patient is treated through a high calorie infusion therapy. These micronutrient metal elements may be used either alone or in combination depending on the state of the patient to be treated. The amounts of the micronutrient metal elements to be added are not particularly limited, as long as the doses (necessary amounts) of the micronutrient metal elements per day are within ordinary ranges. Copper, manganese and zinc are each preferably added in the form of an aqueous solution thereof to the drug solution, and iron is preferably added in the form of a colloid thereof to the drug solution. Manganese and zinc may be mixed with an amino acid solution or a saccharide solution for use.

Micronutrient metal elements such as iron and copper per se are not susceptible to oxidation, but act as catalysts that promote the oxidation of other components. That is, if the micronutrient metal element containing solution is stored in the form of a mixture with an amino acid containing solution or a vitamin containing solution, oxidation and degradation of an amino acid and a vitamin will be accelerated. Therefore, where the micronutrient metal element containing solution is administered together with the amino acid containing solution or the vitamin containing solution, the micronutrient metal element containing solution is preferably contained separately from the amino acid containing solution or the vitamin containing solution, for example, in a multi-chamber container including two or more container portions for storage stability of the drug solution.

The pH of the micronutrient metal element containing solution is preferably adjusted at about 4 to 8, more preferably at about 4.5 to 6, typically by using a pH adjusting agent (e.g., an acid such as hydrochloric acid, acetic acid, lactic acid, malic acid or citric acid, or an alkali such as sodium hydroxide).

In further another preferred embodiment of the inventive reduced-dissolved-oxygen-content drug solution containing pack, an amino acid containing solution, a vitamin containing saccharide solution and a lipid-soluble vitamin containing solution are separately contained in a multi-chamber container including three or more container portions. In this case, the amounts of amino acids, saccharides, vitamins and electrolytes are the same as those described for the reduced-dissolved-oxygen-content drug solution.

For the reduced-dissolved-oxygen-content drug solution containing pack, the drug solution is filled and sealed in the drug solution container and then subjected to the steam sterilization process or the hot water sterilization process, and has a dissolved oxygen concentration of not higher than 2 ppm when the oxygen permeability of the plastic material reaches the steady-state level after the steam sterilization process or the hot water sterilization process.

The drug solution container (drug solution containing pack) in which the drug solution is contained and sealed is subjected to the steam sterilization process or the hot water sterilization process, whereby the drug solution container is heated for a predetermined period. Therefore, the oxygen permeability of the plastic material of the drug solution container can be increased. More specifically, the oxygen permeability of the plastic material of the drug solution container is set at a level not lower than 200 $cm^3/m^2 \cdot 24$ $h \cdot atm$ as measured at a temperature of 25° C. at a humidity of 60% RH within 12 hours after the steam sterilization process or the hot water sterilization process.

The steam sterilization process or the hot water sterilization process is performed on the drug solution container under the same conditions by the same method with the use of the same inert gas as described above. Further, the method for the storage after the steam sterilization process or the hot water sterilization process, the deoxidation means, and the method for the reduction of the dissolved oxygen content with the deoxidation means are the same as those described above.

In the reduced-dissolved-oxygen-content drug solution containing pack, the amount of the oxygen dissolved in the drug solution contained in the drug solution container and the amount of the oxygen present in the head space of the drug solution container can be reduced, whereby the oxidative degradation of the drug solution contained in the drug solution container can be suppressed. Therefore, the reduced-dissolved-oxygen-content drug solution containing pack is advantageous for containing and storing the oxidation-prone drug solutions such as the amino acid containing solution, the vitamin containing saccharide solution, the lipid-soluble vitamin containing solution and the fat emulsion either alone or in combination.

EXAMPLES

The present invention will hereinafter be described by way of inventive examples and comparative examples.

Preparation of Drug Solutions

Formulation 1 (Preparation of Amino Acid Containing Solution)

The following amino acids, the following electrolytes and the following antioxidant were dissolved in injection distilled water, and the pH of the resulting solution was adjusted at 6.8 with succinic acid, followed by nitrogen replacement (bubbling). Further, the following water-soluble vitamins were added to the solution, which was in turn subjected to aseptic filtration. Thus, an amino acid containing solution was prepared.

Components contained in the amino acid containing solution are as follows. Parenthesized values indicate the amounts of the components contained in 300 mL of the amino acid containing solution.

Amino acids: L-leucine (4.2 g), L-isoleucine (2.40 g), L-valine (2.40 g), L-lysine acetate (4.44 g which is equivalent to 3.15 g of L-lysine, L-threonine (1.71 g), L-tryptophan (0.60 g), L-methionine (1.17 g), N-acetyl-L-cysteine (0.40 g which is equivalent to 0.30 g of L-cysteine), L-phenylalanine (2.10 g), L-tyrosine (0.15 g), L-arginine (3.15 g), L-histidine (1.50 g), L-alanine (2.40 g), L-proline (1.50 g), L-serine (0.90 g), L-glycine (1.77 g), L-aspartic acid (0.30 g) and L-glutamic acid (0.30 g)

Electrolytes: calcium chloride (0.37 g which is equivalent to 5.03 mEq of $Ca^{2+}$), magnesium sulfate (0.62 g which is equivalent to 5.03 mEq of $Mg^{2+}$) and potassium acetate (1.08 g which is equivalent to 11.0 mEq of $K^+$)

Water-soluble vitamins: nicotinamide (20 mg) and folic acid (0.2 mg)

Antioxidant: sodium hydrogen sulfite (15 mg)

Formulation 2 (Preparation of Saccharide Solution)

The following saccharide and the following electrolytes were dissolved in injection distilled water, and the pH of the resulting solution was adjusted at 4.0 with acetic acid, followed by nitrogen replacement (bubbling). Further, the following water-soluble vitamins were added to the solution, which was in turn subjected to aseptic filtration. Thus, a saccharide solution was prepared.

Components contained in the saccharide solution are as follows. Parenthesized values indicate the amounts of the components contained in 696 mL of the saccharide solution.

Saccharide: glucose (175 g)

Electrolytes: sodium chloride (2.05 g which is equivalent to 35.0 mEq of $Na^+$), sodium lactate (1.65 g which is equivalent to 14.7 mEq of $Na^+$), potassium chloride (0.746 g which is equivalent to 10.0 mEq/L of $K^+$), potassium iodide (0.083 g which is equivalent to 0.50 mEq of $K^+$) and potassium dihydrogen phosphate (0.821 g which is equivalent to 6.03 mEq of $K^+$) Water-soluble vitamins: thiamine hydrochloride (1.95 mg), pyridoxine hydrochloride (2.45 mg), cyanocobalamin (2.5 μg) and panthenol (7.0 mg)

Formulation 3 (Preparation of Vitamin Containing Solution)

The following lipid-soluble vitamins, and Polysorbate 80 and Polysorbate 20 (each containing a sorbitan fatty acid ester and a nonionic surfactant) were blended together and dissolved in injection distilled water, and then ascorbic acid and biotin were blended in the resulting solution. The pH of the solution was adjusted at 6 to 6.5 with citric acid and sodium hydroxide. Subsequently, sodium riboflavin phosphate was added to the solution, which was in turn subjected to aseptic filtration. Thus, a vitamin containing solution was prepared.

Components contained in the vitamin containing solution are as follows. Parenthesized values indicate the amounts of the components contained in 4 mL of the vitamin containing solution. Lipid-soluble vitamins: vitamin A oil (1650 IU (vitamin A unit), cholecalciferol (0.0025 mg), tocopherol acetate (5.0 mg) and phytonadione (1.0 mg) Water-soluble vitamins: sodium riboflavin phosphate (2.3 mg), ascorbic acid (50 mg) and biotin (0.030 mg)

Nonionic surfactant: Polysorbate 80 (20 mg) and Polysorbate 20 (4 mg)

Formulation 4 (Preparation of Micronutrient metal element Containing Solution)

A colloidizing agent (sodium chondroitin sulfate), iron (III) chloride hexahydrate and sodium hydroxide were blended in injection distilled water. Thus, an iron colloid solution was prepared. Further, solutions respectively prepared by dissolving predetermined amounts of copper sulfate pentahydrate, manganese chloride and zinc sulfate in injection distilled water were blended in the iron colloid solution, and then the pH of the resulting solution was adjusted at 5.5 to 6 with sodium hydroxide. The solution was filtered by an ordinary method. Thus, a micronutrient metal element containing solution was prepared.

Components contained in the micronutrient metal element containing solution and the amounts of the components contained in 4 mL of the micronutrient metal element containing solution are as follows:

Iron (III) chloride hexahydrate: 4.730 mg

Manganese chloride tetrahydrate: 0.09895 mg

Zinc sulfate heptahydrate: 8.625 mg

Copper sulfate pentahydrate: 0.624 mg

Formation of Drug Solution Container

Ingredients of plastic materials for formation of drug solution containers are as follows:

PE-1: An ethylene/1-butene copolymer having a density of 0.940 $g/cm^3$, a water vapor permeability of 7 $g/m^2 \cdot 24$ h (25° C., 90% RH, 20 μm) and available under the trade name of ULTZEX (registered trade mark) 4020B from Prime Polymer Co., Ltd.

PE-2: A mixture of 45 wt % of an ethylene/1-butene copolymer (having a density of 0.920 $g/cm^3$ and available under the trade name of ULTZEX (registered trade mark) 2010 from Prime Polymer Co., Ltd., 50 wt % of an ethylene/1-butene copolymer (having a density of 0.885 $g/cm^3$ and available under the trade name of TOUGHMER (registered trade mark) A0585X from Prime polymer Co., Ltd. and 5 wt % of a polyethylene homopolymer (having a density of 0.965 $g/cm^3$ and available under the trade name of HIGHZEX (registered trade mark) 65150B from Prime Polymer Co., Ltd.

EVOH-1: An ethylene vinyl alcohol having an ethylene content of 27 mol % and available under the trade name of EVAL (registered trade mark) L101 from Kuraray Co., Ltd.

EVOH-2: An ethylene vinyl alcohol having an ethylene content of 44 mol % and available under the trade name of EVAL (registered trade mark) E105 from Kuraray Co., Ltd.

COP: A hydrogenated product of a norbornene ring-opening polymer having a water absorbability of less than 0.01% and available under the trade name of ZEONOA (registered trade mark) from Nippon Zeon Co., Ltd.

PP: A polypropylene having a density of 0.900 g/cm$^3$ and available under the trade name of B355 from Prime Polymer Co., Ltd.

NY: Nylon-6 available under the trade name of AMIRAN (registered trade mark) CM1017 from Toray Industries, Inc.

PE-PP: A mixture of 85 wt % of PE-1 and 15 wt % of a polypropylene homopolymer (having a density of 0.910 g/cm$^3$ and available under the trade name of J103WA from Prime Polymer Co., Ltd.

Adherent PE: An adhesive polyolefin (polyethylene modified with an unsaturated carboxylic acid) having a density of 0.905 g/cm$^3$ and a water vapor permeability of 10 g/m$^2$·24 h (25° C., 90% RH, 20 μm) and available under the trade name of ADMER (registered trade mark) from Prime Polymer Co., Ltd.

PBT: A polybutylene terephthalate having a water vapor permeability of 23 g/m$^2$·24 h (25° C., 90% RH, 10 μm) and available from Mitsubishi Engineering Plastics Corp.

Example 1

(1) Preparation of Small Bag

A 50-μm thick plastic film including an intermediate layer of COP (having a thickness of 10 μm), an inner layer of PE-1 (having a thickness of 20 μm) provided on one of opposite sides of the intermediate layer with respect to a thickness direction, and an outer layer of PE-PP (having a thickness of 20 μm) provided on the other side of the intermediate layer was prepared by a co-extrusion method. The resulting plastic film having a three-layer structure was cut into generally rectangular pieces.

In turn, as shown in FIG. 5, two such generally rectangular plastic film pieces of the three-layer structure were stacked one on the other with their inner layers opposed to each other, and their peripheral edge portions were heat-sealed, whereby a weakly sealed peripheral portion 22 was formed. Thus, a flat and flexible small bag 21 was produced. Then, the small bag 21 was formed with a weakly sealed portion 24 extending parallel to a pair of shorter edges of the weakly sealed peripheral portion 22 between longitudinally middle portions of the longer edges 23 to be thereby partitioned into two compartments 25, 26.

The longer edges 23 of the weakly sealed peripheral portion 22 of the small bag 21 each had an unsealed portion communicating with the compartment 25, 26. The unsealed portion serves as a filling port through which the drug solution was filled in the compartment 25, 26.

Then, 4 mL of the vitamin containing solution of Formulation 3 was filled in one compartment 25 through the filling port communicating with the compartment 25, and then this filling port was heat-sealed in a nitrogen atmosphere. Further, 4 mL of the micronutrient metal element containing solution of Formulation 4 was filled in the other compartment 26 through the filling port communicating with the compartment 26, and then this filling port was heat-sealed in the nitrogen atmosphere.

(2) Production of Drug Solution Container and Drug Solution Containing Pack

A plastic film (see FIG. 1) having a seven-layer structure including layers shown in the column of "Sample 1" in Table 1 was prepared by a co-extrusion method.

In turn, as shown in FIG. 5, two generally rectangular plastic film pieces were cut out of the plastic film of the seven-layer structure and stacked one on the other with their innermost layers opposed to each other, and then their peripheral edge portions were heat-sealed to form a heavily sealed peripheral portion 16. Further, a weakly sealed portion 18 was formed as extending between longitudinally middle portions of a pair of heavily sealed longitudinal side portions 17 of the heavily sealed peripheral portion 16. Thus, a container portion defined by the heavily sealed peripheral portion 16 was partitioned into a first container portion 19 and a second container portion 20.

It is noted that the small bag 21 produced in the aforementioned manner (1) was inserted in a second container portion formation region before the formation of the heavily sealed peripheral portion 16, and an outer surface portion of the small bag 21 adjacent to one longer edge 23 and an inner surface portion of the second container portion 20 adjacent to the weakly sealed portion 18 were heat-sealed to be fixed with each other.

Tube members 13 for ejection and injection of the drug solutions were provided in the heavily sealed peripheral portion 16 so as to respectively communicate with the first container portion 19 and the second container portion 20, and had unsealed portions for the communication with the first container portion 19 and the second container portion 20. The unsealed portions were defined as filling ports for filling drug solutions into the first container portion 19 and the second container portion 20, respectively.

In turn, 300 mL of the amino acid containing solution of Formulation 1 was filled in the first container portion 19, and 696 mL of the saccharide solution of Formulation 2 was filled in the second container portion 20 in a nitrogen atmosphere, and then the unsealed portions were heat-sealed. Thus, a drug solution containing pack having a total drug solution amount of 1004 mL was obtained. The drug solution containing pack had ahead space having a volume of about 30 mL, and gas in the head space was replaced with nitrogen (about 50%), so that the head space had an oxygen concentration of 10%.

(3) Steam Sterilization Process and Dissolved Oxygen Content Reducing Process

The drug solution containing pack obtained in the aforementioned manner (2) was put in a sterilization pot, and heated in a water-vapor-saturated nitrogen atmosphere (at a temperature of 110° C. at a pressure of 2700 hPa) for 30 minutes, whereby a high pressure steam sterilization process was performed. The oxygen concentration of the nitrogen atmosphere was regulated at not higher than 2%.

Then, the drug solution containing pack subjected to the steam sterilization process was stored together with an oxygen scavenger (available under the trade name of AGELESS (registered trade mark) from Mitsubishi Gas Chemical Company Inc. in an outer bag for 20 days.

The outer bag was composed of a multi layer film of a three-layer structure including an inner layer of a polyethylene, an intermediate layer of a polyvinyl alcohol and an outer layer of a drawn polypropylene. The bag had an oxygen permeability of not higher than 0.1 cm$^3$/m$^2$·24 h·atm at a temperature of 25° C. at a humidity of 60% RH, and a water vapor permeability of 0.5 g/m$^2$·24 h at a temperature of 25° C. at a humidity of 90% RH. The outer bag had an inner space volume of about 300 to about 500 mL, and had an internal oxygen concentration adjusted at not higher than 2% by nitrogen replacement. The drug solution bag was accommodated and sealed in the outer bag within one hour after the high pressure steam sterilization process.

Example 2

A plastic film (see FIG. 2) of a six-layer structure including layers shown in the column of "Sample 2" in Table 1 was prepared by a co-extrusion method.

In turn, a drug solution containing pack was produced in substantially the same manner as in Example 1-(2), except that two such plastic films of the six layer structure were used. Then, the steam sterilization process and the dissolved oxygen content reducing process were performed in the same manner as in Example 1-(3).

Example 3

A plastic film (see FIG. 1) of a seven-layer structure including layers shown in the column of "Sample 3" in Table 1 was prepared by a co-extrusion method. A layered structure including a protective layer 5 and an adhesive layer 7 of the multilayer film had a water vapor permeability of 4.1 g/m²·24 h (at 25° C. and 90% RH).

In turn, a drug solution containing pack was produced in substantially the same manner as in Example 1-(2), except that two such plastic films of the seven layer structure were used. Then, the steam sterilization process and the dissolved oxygen content reducing process were performed in the same manner as in Example 1-(3).

Example 4

A plastic film (see FIG. 1) of a seven-layer structure including layers shown in the column of "Sample 4" in Table 2 was prepared by a co-extrusion method. A layered structure including a protective layer 5 and an adhesive layer 7 of the multilayer film had a water vapor permeability of 7.0 g/m² 24 h (at 25° C. and 90% RH).

In turn, a drug solution containing pack was produced in substantially the same manner as in Example 1-(2), except that two such plastic films of the seven layer structure were used.

Further, the steam sterilization process and the dissolved oxygen content reducing process were performed in substantially the same manner as in Example 1-(3), except that an outer bag produced from a multilayer film of a three-layer structure including an intermediate layer of an ethylene/vinyl alcohol copolymer and an inner layer and an outer layer of a polyethylene and having an oxygen permeability of 0.5 cm³/m²·24 h·atm at a temperature of 25° C. at a humidity of 60% RH and an oxygen permeability of 3 cm³/m²·24 h·atm at a temperature of 25° C. at a humidity of 90% RH was used.

Example 5

A plastic film (see FIG. 2) of a six-layer structure including layers shown in the column of "Sample 5" in Table 2 was prepared by a co-extrusion method. A layered structure including a protective layer 5 and an adhesive layer 7 of the multilayer film had a water vapor permeability of 5.1 g/m²·24 h (at 25° C. and 90% RH).

In turn, a drug solution containing pack was produced in substantially the same manner as in Example 1-(2), except that two such plastic films of the six layer structure were used. Then, the steam sterilization process and the dissolved oxygen content reducing process were performed in the same manner as in Example 1-(3).

Example 6

A plastic film (see FIG. 1) of a seven-layer structure including layers shown in the column of "Sample 6" in Table 2 was prepared by a co-extrusion method. A layered structure including a protective layer 5 and an adhesive layer 7 of the multilayer film had a water vapor permeability of 3.2 g/m²·24 h (at 25° C. and 90% RH).

In turn, a drug solution containing pack was produced in substantially the same manner as in Example 1-(2), except that two such plastic films of the seven layer structure were used. Further, the steam sterilization process and the dissolved oxygen content reducing process were performed in the same manner as in Example 1-(3).

Comparative Example 1

A plastic film (see FIG. 1) of a seven-layer structure including layers shown in the column of "Comparative Sample 1" in Table 3 was prepared by a co-extrusion method.

In turn, a drug solution containing pack was produced in substantially the same manner as in Example 1-(2), except that two such plastic films of the seven layer structure were used. Further, the steam sterilization process and the dissolved oxygen content reducing process were performed in the same manner as in Example 1-(3).

Comparative Example 2

A plastic film of a five-layer structure including layers shown in the column of "Comparative Sample 2" in Table 3 and having no adhesive layer was prepared by a co-extrusion method.

In turn, a drug solution containing pack was produced in substantially the same manner as in Example 1-(2), except that two such plastic films of the five layer structure were used. Further, the steam sterilization process and the dissolved oxygen content reducing process were performed in the same manner as in Example 1-(3).

Evaluation Test for Dissolved Oxygen Content Reducing Process

The surface of each of the drug solution containing packs subjected to the high pressure steam sterilization process was dehumidified by hot air at about 40° C. for one minute. Further, the drug solution containing pack was allowed to stand in an environment at a temperature of 25° C. at a humidity of 60% RH, and then the oxygen concentration of the drug solution in the drug solution containing pack was measured by a nondestructive oxygen concentration meter (available under the trade name of Fibox 3 from PreSens GmbH). The measurement of the oxygen concentration was carried out after a lapse of six hours from the steam sterilization process, and then every day after the steam sterilization process. For the measurement of the oxygen permeability, an apparatus available under the trade name of OX-TRAN (registered trademark) from MOCON, Inc. was used.

As a result, the oxygen concentrations of the drug solutions contained in the drug solution containing packs of Examples and Comparative Examples were reduced to not higher than 2 ppm after a lapse of about seven days from the accommodation and sealing of the drug solution containing pack in the outer bag.

The results of the measurement of the oxygen permeability of each of the multilayer films used in Examples and Comparative Examples are shown in Tables 1 to 3.

TABLE 1

| | Sample | | |
|---|---|---|---|
| | 1 | 2 | 3 |
| Layers of multilayer film | | | |
| (Outer side O) | | | |
| Protective layer 5 | PE-1 (20 μm) | PE-1 (20 μm) | PE-1 (20 μm) |
| Adhesive layer 7 | Adherent PE (20 μm) | Adherent PE (20 μm) | Adherent PE (20 μm) |
| Intermediate layer 4 | EVOH-1 (5 μm) | EVOH-2 (5 μm) | EVOH-1 (15 μm) |
| Adhesive layer 6 | Adherent PE (20 μm) | Adherent PE (20 μm) | Adherent PE (20 μm) |
| Less water-absorptive layer 3 | COP (10 μm) | — | COP (10 μm) |
| Polyethylene layer 2 | PE-2 (145 μm) | PE-2 (155 μm) | PE-2 (130 μm) |
| Seal layer 1 | PE-PP (30 μm) | PE-PP (30 μm) | PE-PP (30 μm) |
| (Outer side I) | | | |
| Water vapor permeability (Protective layer 5 + Adhesive layer 7) | 4.1 | 4.1 | 4.1 |
| Overall thickness of multilayer film | 250 μm | 250 μm | 250 μm |
| Oxygen permeability | | | |
| Steady state | 5 | 20 | 1 |
| 6 hours after sterilization process | 800 | 800 | 500 |

TABLE 2

| | Sample | | |
|---|---|---|---|
| | 4 | 5 | 6 |
| Layers of multilayer film | | | |
| (Outer side O) | | | |
| Protective layer 5 | PBT-1 (10 μm) | PE-1 (16 μm) | PE-1 (30 μm) |
| Adhesive layer 7 | Adherent PE (20 μm) | Adherent PE (16 μm) | Adherent PE (20 μm) |
| Intermediate layer 4 | EVOH-1 (5 μm) | EVOH-1 (4 μm) | EVOH-1 (5 μm) |
| Adhesive layer 6 | Adherent PE (20 μm) | Adherent PE (16 μm) | Adherent PE (20 μm) |
| Less water-absorptive layer 3 | COP (10 μm) | — | COP (10 μm) |
| Polyethylene layer 2 | PE-2 (155 μm) | PE-2 (124 μm) | PE-2 (175 μm) |
| Seal layer 1 | PE-PP (30 μm) | PE-PP (24 μm) | PE-PP (40 μm) |
| (Outer side I) | | | |
| Water vapor permeability (Protective layer 5 + Adhesive layer 7) | 7.0 | 5.1 | 3.2 |
| Overall thickness of multilayer film | 250 μm | 250 μm | 250 μm |
| Oxygen permeability | | | |
| Steady state | 5 | 25 | 5 |
| 6 hours after sterilization process | 200 | 1000 | 500 |

TABLE 3

| | Comparative Sample | |
|---|---|---|
| | 1 | 2 |
| Layers of multilayer film | | |
| (Outer side O) | | |
| Protective layer 5 | PE-1 (20 μm) | PE-1 (20 μm) |
| Adhesive layer 7 | Adherent PE (20 μm) | — |
| Intermediate layer 4 | NY (5 μm) | PE-2 (100 μm) |
| Adhesive layer 6 | Adherent PE (20 μm) | — |
| Less water-absorptive layer 3 | COP (10 μm) | PP (10 μm) |
| Polyethylene layer 2 | PE-2 (145 μm) | PE-2 (100 μm) |
| Seal layer 1 | PE-PP (30 μm) | PE-PP (30 μm) |
| (Outer side I) | | |
| Water vapor permeability (Protective layer 5 + Adhesive layer 7) | 4.1 | — |
| Overall thickness of multilayer film | 250 μm | 260 μm |
| Oxygen permeability | | |
| Steady state | 270 | 900 |
| 6 hours after sterilization process | — | — |

In each cell of "Layers of Multilayer Film" in Tables 1 to 3, the type of the plastic material for each layer is shown in an upper line, and the thickness of the layer is shown in a parenthesized form in a lower line. Further, the unit of the water vapor permeability is $g/m^2 \cdot 24$ h, and the unit of the oxygen permeability is $cm^3/m^2 \cdot 24$ h·atm.

While the present invention has been described by way of exemplary embodiments thereof, these embodiments are merely illustrative but not restrictive. It should be understood that modifications of the present invention apparent to those skilled in the art fall within the scope of the appended claims.

INDUSTRIAL APPLICABILITY

The reduced-dissolved-oxygen-content drug solution and the production method therefor according to the present invention are advantageous for stably storing the amino acid containing solution, the vitamin containing saccharide solution, the lipid-soluble vitamin containing solution, the fat emulsion and the like for a long period of time. The reduced-dissolved-oxygen-content drug solution containing pack according to the present invention is advantageous for containing and storing the oxidation-prone drug solutions such as the amino acid containing solution, the vitamin containing saccharide solution, the lipid-soluble vitamin containing solution, the vitamin containing solution and the fat emulsion either alone or in combination.

What is claimed is:

1. A drug solution container containing a drug solution with a reduced dissolved oxygen content,
the drug solution being contained and sealed in the drug solution container formed of a plastic material having an oxygen permeability of not lower than 200 $cm^3/m^2 \cdot 24$ h·atm at a temperature of 25° C. at a humidity of 60% RH within 12 hours after a steam sterilization process or a hot water sterilization process and having a steady-state oxygen permeability of not higher than 100 cm$^3$/m$^2$·24 h·atm at a temperature of 25° C. at a humidity of 60% RH, the drug solution having been subjected to the steam sterilization process or the hot water sterilization process, and the drug solution having a dissolved oxygen concentration of not higher than 2 ppm when the oxygen permeability of the plastic material reaches the steady-state level after the steam sterilization process or the hot water sterilization process, wherein the drug solution container is wrapped with an outer package having an oxygen barrier property of defining an environment having deoxidization means between the outer package and the drug solution container, the drug solution is stored in the environment having deoxidization means after the steam sterilization process or the hot water sterilization process, the plastic material forming the drug solution container is a multilayer film having a sealing layer at an inner surface side of the drug solution container, a protective layer on an outer surface side of the drug solution container, an intermediate layer made of polyol-based plastic between the sealing layer and the protective layer and a less water-absorptive layer made of polycycloolefin between the sealing layer and the intermediate layer, and the protective layer is a polyolefin resin or a polyester resin having a water vapor permeability of 1 to 50 g/m$^2$·24 h at a temperature of 25° C. at a humidity of 90% RH.

2. The drug solution container as set forth in claim 1, which comprises an oxidation-prone drug solution.

3. The drug solution container as set forth in claim 1, which comprises at least one solution selected from the group consisting of an amino acid containing solution, a vitamin containing saccharide solution and a lipid-soluble vitamin containing solution.

4. The drug solution container as set forth in claim 3, wherein the amino acid containing solution contains at least one amino acid selected from the group consisting of L-leucine, L-isoleucine, L-valine, L-lysine, L-threonine, L-tryptophan, L-methionine, L-cysteine, L-phenylalanine, L-tyrosine, L-arginine, L-histidine, L-alanine, L-proline, L-serine, glycine, L-aspartic acid and L-glutamic acid.

5. The drug solution container as set forth in claim 3, wherein the vitamin containing saccharide solution contains a saccharide, and a water-soluble vitamin selected from the group consisting of vitamin $B_1$, vitamin $B_2$, vitamin $B_6$, vitamin $B_{12}$, vitamin C, folic acid, niacin, biotin and a pantothenic compound.

6. The drug solution container as set forth in claim 3, wherein the lipid-soluble vitamin containing solution contains at least one lipid-soluble vitamin selected from the group consisting of vitamin A, vitamin D, vitamin E and vitamin K.

7. A production method for a drug solution container containing a drug solution with a reduced dissolved oxygen content, the method comprising the steps of:

filling and sealing a drug solution in a drug solution container formed of a plastic material having an oxygen permeability of not lower than 200 cm$^3$/m$^2$·24 h·atm at a temperature of 25° C. at a humidity of 60% RH within 12 hours after a steam sterilization process or a hot water sterilization process and having a steady-state oxygen permeability of not higher than 100 cm$^3$/m$^2$·24 h·atm at a temperature of 25° C. at a humidity of 60% RH;

subjecting the drug solution container to a steam sterilization process or a hot water sterilization process; and reducing a dissolved oxygen concentration of the drug solution to not higher than 2 ppm by storing the drug solution container in an environment having deoxidization means defined by wrapping the drug solution container with an outer package having an oxygen barrier property until the oxygen permeability of the plastic material reaches the steady-state level, wherein the plastic material forming the drug solution container is a multilayer film having a sealing layer at an inner surface side of the drug solution container, a protective layer on an outer surface side of the drug solution container, an intermediate layer made of polyol-based plastic between the sealing layer and the protective layer and a less water-absorptive layer made of polycycloolefin between the sealing layer and the intermediate layer, and the protective layer is a polyolefin resin or a polyester resin having a water vapor permeability of 1 to 50 g/m$^2$·24 h at a temperature of 25° C. at a humidity of 90% RH.

8. The production method as set forth in claim 7, wherein the deoxidization means is an oxygen scavenger.

9. A drug solution containing pack with a reduced dissolved oxygen content, comprising:

a drug solution container formed of a plastic material having an oxygen permeability of not lower than 200 cm$^3$/m$^2$·24 h·atm at a temperature of 25° C. at a humidity of 60% RH within 12 hours after a steam sterilization process or a hot water sterilization process and having a steady-state oxygen permeability of not higher than 100 cm$^3$/m$^2$·24 h·atm at a temperature of 25° C. at a humidity of 60% RH;

a drug solution contained and sealed in the drug solution container; and an outer package with an oxygen barrier property wrapping the drug solution container and defining an environment having deoxidization means between the outer package and the drug solution container;

wherein the drug solution contained and sealed in the drug solution container has been subjected to the steam sterilization process or the hot water sterilization process, and to a deoxidization process for reducing a dissolved oxygen concentration of the drug solution to not higher than 2 ppm when the oxygen permeability of the plastic material reaches the steady-state level after the steam sterilization process or the hot water sterilization process, the drug solution is stored in the environment having deoxidization means after the steam sterilization process or the hot water sterilization process, the plastic material forming the drug solution container is a multilayer film having a sealing layer at an inner surface side of the drug solution container, a protective layer on an outer surface side of the drug solution container, an intermediate layer made of polyol-based plastic between the sealing layer and the protective layer and a less water-absorptive layer made of polycycloolefin between the sealing layer and the intermediate layer, and the protective layers polyolefin resin or a polyester resin having a water vapor permeability of 1 to 50 g/m$^2$·24 h at a temperature of 25° C. at a humidity of 90% RH.

10. A reduced-dissolved-oxygen-content drug solution containing pack as set forth in claim 9,
wherein the drug solution comprises an oxidation-prone drug solution.

11. A reduced-dissolved-oxygen-content drug solution containing pack as set forth in claim 10,
wherein the drug solution comprises at least one solution selected from the group consisting of an amino acid containing solution, a vitamin containing saccharide solution and a lipid-soluble vitamin containing solution.

12. A reduced-dissolved-oxygen-content drug solution containing pack as set forth in claim 9,
wherein the drug solution container includes a plurality of container portions isolated from each other by a removable partition,
wherein an amino acid containing solution is contained in one of the container portions, and a saccharide solution is contained in another one of the container portions.

13. A reduced-dissolved-oxygen-content drug solution containing pack as set forth in claim 9,
wherein the drug solution container includes a plurality of container portions isolated from each other by a removable partition,
wherein one of the container portions is a small bag provided in another one of the container portions.

14. A reduced-dissolved-oxygen-content drug solution containing pack as set forth in claim 13,
wherein a lipid-soluble vitamin containing solution or a fat emulsion is contained in the small bag.

15. A reduced-dissolved-oxygen-content drug solution containing pack as set forth in claim 13,
wherein the small bag is partitioned into two compartments,
wherein a lipid-soluble vitamin containing solution is contained in one of the two compartments, and a micronutrient metal element drug solution is contained in the other compartment.

16. A reduced-dissolved-oxygen-content drug solution containing pack as set forth in claim 11,
wherein the amino acid containing solution contains at least one amino acid selected from the group consisting of L-leucine, L-isoleucine, L-valine, L-lysine, threonine, L-tryptophan, L-methionine, L-cysteine, L-phenylalanine, L-tyrosine, L-arginine, L-histidine, L-alanine, L-proline, L-serine, glycine, L-aspartic acid and L-glutamic acid.

17. A reduced-dissolved-oxygen-content drug solution containing pack as set forth in claim 11,
wherein the vitamin containing saccharide solution contains a saccharide, and at least one water-soluble vitamin selected from the group consisting of vitamin $B_1$, vitamin $B_2$, vitamin $B_6$, vitamin $B_{12}$, vitamin C, folic acid, niacin, biotin and a pantothenic compound.

18. A reduced-dissolved-oxygen-content drug solution containing pack as set forth in claim 11,
wherein the lipid-soluble vitamin containing solution contains at least one lipid-soluble vitamin selected from the group consisting of vitamin A, vitamin D, vitamin E and vitamin K.

19. A reduced-dissolved-oxygen-content drug solution containing pack as set forth in claim 15,
wherein the micronutrient metal element drug solution contains at least one element selected from the group consisting of iron, manganese, zinc, copper, selenium, molybdenum, cobalt and chromium.

20. A reduced-dissolved-oxygen-content drug solution containing pack as set forth in claim 12,
wherein the plurality of container portions isolated from each other by the removable partition includes two container portions disposed in opposed relation on opposite sides of the removable partition, and a small bag disposed in one of the two container portions,
wherein the small bag is further partitioned into two compartments,
wherein an amino acid containing solution which contains at least one amino acid selected from the group consisting of L-leucine, L-isoleucine, L-valine, L-lysine, L-threonine, L-tryptophan, L-methionine, L-cysteine, L-phenylalanine, L-tyrosine, L-arginine, L-histidine, L-alanine, L-proline, L-serine, glycine, L-aspartic acid and L-glutamic acid is contained in the one container portion,
wherein a vitamin containing saccharide solution which contains a saccharide and at least one water-soluble vitamin selected from the group consisting of vitamin $B_1$, vitamin $B_2$, vitamin $B_6$, vitamin $B_{12}$, vitamin C, folic acid, niacin, biotin and a pantothenic compound is contained in the other container portion,
wherein a lipid-soluble vitamin containing solution which contains at least one lipid-soluble vitamin selected from the group consisting of vitamin A, vitamin D, vitamin E and vitamin K is contained in one of the compartments of the small bag,
wherein a micronutrient metal element drug solution containing at least one element selected from the group consisting of iron, manganese, zinc, copper, selenium, molybdenum, cobalt and chromium is contained in the other compartment of the small bag.

21. A reduced-dissolved-oxygen-content drug solution containing pack as set forth in claim 20,
wherein a solution mixture obtained by mixing the solutions contained in the two container portions and the two compartments contains 0.4 to 20.0 g/L of L-leucine, 0.2 to 14.0 g/L of L-isoleucine, 0.1 to 16.0 g/L of L-valine, 0.2 to 14.0 g/L of L-lysine, 0.1 to 8.0 g/L of L-threonine, 0.04 to 3.0 g/L of L-tryptophan, 0.1 to 8.0 g/L of L-methionine, 0.01 to 2.0 g/L of L-cysteine, 0.2 to 12.0 g/L of L-phenylalanine, 0.01 to 2 g/L of L-tyrosine, 0.2 to 14.0 g/L of L-arginine, 0.1 to 8.0 g/L of L-histidine, 0.2 to 14.0 g/L of L-alanine, 0.1 to 10.0 g/L of L-proline, 0.1 to 6.0 g/L of L-serine, 0.1 to 12.0 g/L of glycine, 0.01 to 4.0 g/L of L-aspartic acid, 0 to 6.0 g/L of L-glutamic acid, 20 to 800 g/L of glucose, 400 to 6500 IU/L of vitamin A, 0.5 to 10.0 µg/L of cholecalciferol as vitamin D, 1.0 to 20.0 mg/L of tocopherol acetate as vitamin E, 0.2 to 4.0 mg/L of phytonadione as vitamin K, 0.4 to 30.0 mg/L of thiamine hydrochloride as vitamin $B_1$, 0.5 to 6.0 mg/L of riboflavin as vitamin $B_2$, 0.5 to 8.0 mg/L of pyridoxine hydrochloride as vitamin $B_6$, 0.5 to 50.0 µg/L of cyanocobalamin as vitamin $B_{12}$, 5.0 to 80.0 mg/L of nicotinamide as a nicotinic compound, 1.5 to 35.0 mg/L of pantothenic acid as a pantothenic compound, 50 to 800 µg/L of folic acid, 12 to 200 mg/L of ascorbic acid as vitamin C, 5 to 120 µg/L of biotin, 10 to 160 mEq/L of sodium ions, 1 to 40 mEq/L of magnesium ions, 5 to 80 mEq/L of potassium ions, 1 to 40 mEq/L of calcium ions, 10 to 160 mEq/L of chloride ions, 0 to 5 mEq/L of iodide ions, and 1 to 40 mmol/L of phosphate ions.

* * * * *

UNITED STATES PATENT AND TRADEMARK OFFICE
CERTIFICATE OF CORRECTION

Page 1 of 1

PATENT NO.        : 9,901,513 B2
APPLICATION NO.   : 12/447101
DATED             : February 27, 2018
INVENTOR(S)       : Sumiyoshi et al.

It is certified that error appears in the above-identified patent and that said Letters Patent is hereby corrected as shown below:

Claim 16, Column 37, Lines 43-44, "threonine" should read --L-threonine--

Signed and Sealed this
Seventeenth Day of July, 2018

Andrei Iancu
*Director of the United States Patent and Trademark Office*